United States Patent
Shou-Cang et al.

(10) Patent No.: US 9,155,814 B2
(45) Date of Patent: Oct. 13, 2015

(54) NANOSTRUCTURED MATERIAL FORMULATED WITH BONE CEMENT FOR EFFECTIVE ANTIBIOTIC DELIVERY

(75) Inventors: Shen Shou-Cang, Jurong Island (SG); Ng Wai Kiong, Jurong Island (SG); Leonard Chia, Jurong Island (SG); Reginald Tan, Jurong Island (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 13/486,382

(22) Filed: Jun. 1, 2012

(65) Prior Publication Data

US 2012/0308633 A1  Dec. 6, 2012

Related U.S. Application Data

(63) Continuation of application No. PCT/SG2010/000453, filed on Dec. 3, 2010.

(60) Provisional application No. 61/412,566, filed on Nov. 11, 2010, provisional application No. 61/266,995, filed on Dec. 4, 2009.

(51) Int. Cl.

| *A61K 9/14* | (2006.01) |
| *A61P 31/04* | (2006.01) |
| *A61L 24/00* | (2006.01) |
| *A61L 27/54* | (2006.01) |
| *A61L 24/06* | (2006.01) |
| *A61K 47/48* | (2006.01) |
| *C08L 33/12* | (2006.01) |

(52) U.S. Cl.
CPC ............ *A61L 24/0036* (2013.01); *A61L 24/001* (2013.01); *A61L 24/0068* (2013.01); *A61L 24/06* (2013.01); *A61L 27/54* (2013.01); *A61K 47/48861* (2013.01); *A61L 2300/406* (2013.01); *A61L 2400/12* (2013.01); *A61L 2430/02* (2013.01); *C08L 33/12* (2013.01)

(58) Field of Classification Search
CPC . A61L 27/54; A61L 2400/12; A61L 24/0036; A61L 24/001; A61L 2300/406; A61L 2400/06; A61L 2430/02; A61K 2300/00; A61K 9/0024; A61K 47/48861; B82Y 5/00; C08L 33/12
USPC .................................................. 424/423, 489
See application file for complete search history.

(56) References Cited

U.S. PATENT DOCUMENTS

| 4,843,112 | A | * | 6/1989 | Gerhart et al. ................. 523/114 |
| 4,869,906 | A | | 9/1989 | Dingeldein et al. |
| 6,599,961 | B1 | * | 7/2003 | Pienkowski et al. .......... 523/120 |
| 2006/0292199 | A1 | * | 12/2006 | Kuhn et al. .................... 424/422 |
| 2007/0160639 | A1 | * | 7/2007 | Pantelidis et al. ............. 424/423 |

OTHER PUBLICATIONS

Slowing et al. Mesoporous silica nanoparticles as controlled release drug delivery and gene transfection carriers. Apr. 10, 2008. Advanced Drug Delivery Reviews. pp. 1278-1288.*
NHS Choices. Preventing Osteomyelitis. Date accessed: Mar. 10, 2014.*

* cited by examiner

*Primary Examiner* — Frederick Krass
*Assistant Examiner* — Tracy Liu
(74) *Attorney, Agent, or Firm* — Kilpatrick Townsend & Stockton LLP

(57) ABSTRACT

This invention uses mesoporous silica nanoparticles and other nanostructured materials to formulate polyacrylate-based bone cement for achieving an enhanced and controlled elution of active ingredients such as antibiotics. This invention overcomes the limitation of low antibiotic release from commercial polyacrylate-based bone cements using for example, PMMA. In certain aspects, the formulation enables a sustained release of antibiotics from the bone cement over a period of 80 days and achieves 70% of total drug release, whereas the commercial antibiotic bone cement (e.g., Smart-Set GHV) only releases about 5% of the antibiotics on the first day and subsequently an almost negligible amount. In addition, the mechanical properties of our formulated bone cements are well retained. The inventive bone cement exhibits good antibacterial properties and has very low cytotoxicity to mouse fibroblast cells.

19 Claims, 19 Drawing Sheets

Gentamicin release profiles from Gentamicin loaded MSN formulated bone cement.

Gentamicin release profiles from Gentamicin loaded MSN formulated bone cements

Antibacterial property of Gentimicin loaded MSN formulated bone cement compared to commercially available antibiotic loaded bone cement SMARTSET-GHV

NANOSTRUCTURED MATERIAL FORMULATED WITH BONE CEMENT FOR EFFECTIVE ANTIBIOTIC DELIVERY

CROSS-REFERENCE TO RELATED APPLICATIONS

The present application is a Continuation patent application of International Patent Application No. PCT/SG2010/000453, filed Dec. 3, 2010, and claims priority to U.S. Provisional Application Nos. 61/266,995, filed Dec.4, 2009 and 61/412,566, filed Nov.11, 2010 the disclosures of which are herein incorporated by reference in their entirety for all purposes.

BACKGROUND OF THE INVENTION

Currently total hip and knee joint replacements (arthroplasty) are the most common major orthopedic surgical procedures, with approximately 1 million performed world-wide annually. A major proportion of these prostheses are anchored to the contiguous cancellous bone in an acrylic based bone cement, which serves to immobilize the implant and distribute force from it to the adjoining bone. (see, Lewis, G., *J. Biomed. Mater. Res. B. Appl. Biomater.*, 38:155-182 (1997); Lewis, G., *J. Biomed. Mater. Res. B. Appl. Biomater.*, 84:301-319 (2007); Lewis, G., *J. Biomed. Mater. Res. B. Appl. Biomater.*, 89:558-574 (2009)).

Despite strict antiseptic operative procedure deployed against infection, postoperative osteomyelitis remains a considerable problem in orthopedic surgery. The infection rates of joint replacement range from 1-3% after surgery operation. For infected cases, total removal of the implant is often necessary and usually leads to severe functional disability. Such infections are very costly in terms of quality of life and public health expenditure. In order to reduce the risk of post-operative infection, it is of great interest to release antibiotics at the implanted local site (see FIG. 1). The main goals of the drug releasing systems are to maintain drug levels at the desired therapeutic range with just a single dose and to localize delivery of the drug to a specific body compartment, thereby reducing the need for follow-up care and increasing patient comfort and/or compliance.

There are over 30 commercially available basic acrylic bone cements for use in cemented arthoplasties. Some of the most widely used brands are Simplex P (Styker Co.), Palacos R (Heraeus Kulzer), SmartSet HV (DePuy Co.) and Vertefix Radiopaque (Cook Medical). In general, all brands contain polymer powder and liquid monomer components that are mixed together to form a dough-like bone cement. The polymer powder consists of prepolymerized poly(methyl methacrylate) ("PMMA") beads or a PMMA-based polymer; benzoyl peroxide as the initiator of the polymerization reaction; and a radiopacifier of barium sulfate or zirconium dioxide. The liquid monomer comprises of methyl methacrylate monomer; N,N-dimethyl-p-toludine (DMPT) as the accelerator of the polymerization reaction; and hydroquinone as an inhibitor of that reaction.

To date, the commercially available antibiotic delivery systems (e.g., SmartSet GHV (DePuy Co.); Simplex P with Tobramycin (Stryker)) are based on antibiotic loaded poly (methyl methacrylate) (PMMA) bone cement. The main problem of the current composite bone cements is their inability to maintain sustained drug release for several weeks at the site of implantation. These drug delivery systems are based on the method of loading the drug agents into the polymer and/or monomer components of the cement by mechanical mixing or by adsorption directly into the matrices of polymer (see Padilla et al. *J. Controlled Release*, 83:343-52 (2002); Anagnostakos, K. and Kelm J., *J. Biomed. Mater. Res. B. Appl. Biomater.*, 90B:467-475-182 (2009)). However, such techniques do not achieve sustained drug release at the implanted site for more than a few days. At initial stages following surgery, the typical bone cements elute antibiotics located at the surface of the interface between the cement and the adjacent tissue or medium, and not the sub-layers of the bone cement. The diffusion of drug becomes more limited in the later stages. As more than 90% of the antibiotic may be retained within the PMMA matrix, the bone cement cannot function to protect the surrounding tissue from infection.

Recent advancements in the design and development of mesoporous nanomaterials have highlighted their potential for drug delivery. These nanomaterials are characterized by high relative surface areas, tunable pore volumes, controllable surface functionalities, and well-ordered pore structures. FIG. 2 depicts a microscopy image of the organized structure of mesoporous nanorods. Examples of mesoporous nanomaterials include mesoporous silica nanoparticles, alumina nanofibers, carbon nanotubes, titania nanotubes, hydroxyapatite nanorods, and hydroxyapatite nanoparticles. Mesoporous silica nanoparticles (MSN) have large specific pore volumes (e.g., range from 0.6-1 $cm^3/g$) and high surface areas (e.g., range of 700-1000 $m^2/g$), making it possible to load the nanoparticles with drug and reach loading levels that exceed 30 wt % (see, Gao et al., *J. Phys. Chem. B.*, 113:1796-804 (2009); Vellet-Regi et al., *J. Intern Med.*, 267:22-43 (2009); Rosenholm et al., *Nanoscale*, 2:1870-83 (2010)).

In view of the foregoing developments, there is a need to develop bone cements with improved sustain release of antibiotics. The present invention satisfies this and other needs.

BRIEF SUMMARY OF THE INVENTION

The present invention provides in-part, mesoporous silica nanoparticles and other nanostructured materials as drug carriers and formulations with for example, PMMA-based bone cement, to improve the drug release property from an antibiotic load bone cement. The uniformly arrayed one-dimensional pore structure builds up effective diffusion channels in a PMMA matrix to facilitate drug molecules diffusion to the surface of the bone cement (see FIG. 3). In fact, a sustained release of simultaneous loading active substances can be achieved.

In one embodiment, the present invention provides a bone cement, the bone cement comprising:
  a polyacrylate; and
  an active pharmaceutical ingredient, wherein the active pharmaceutical ingredient is disposed within a mesoporous material.

In one aspect, the polyacrylate comprises polymerized methyl methacrylate. Preferably, the polyacrylate is poly(methyl methacrylate). Alternatively, or more preferably, the polyacrylate is in the form of a powder. In certain aspects, the polyacrylate is a commercially available bone cement (e.g., PMMA-based bone cement) that has been optionally further polymerized with a monomer such as an acrylate monomer (e.g., methyl methacrylate). In a preferred aspect, the bone cement comprises diffusion channels in a PMMA matrix to facilitate drug molecules diffusion to the surface of the bone cement. In certain aspects, the inventive bone cement is a mesoporous material incorporated bone cement.

In a second embodiment, the invention provides a method for preparing a bone cement, said method comprising:

a) impregnating a mesoporous material with an active pharmaceutical agent to produce an impregnated mesoporous material;

b) mixing the impregnated mesoporous material with a polyacrylate to produce an admixture;

c) adding a monomer to the admixture; and d) polymerizing the admixture to form the bone cement.

In a first aspect, the step of mixing a mesoporous material with the polyacrylate comprises mixing a solid comprising the mesoporous material and a second solid comprising the polyacrylate.

In certain aspects, the step of mixing the mesoporous material with the polyacrylate comprises dispersing the impregnated mesoporous material and the polyacrylate in a suspension.

In a third embodiment, the present invention provides a method for preparing a bone cement, the method comprising the steps of:

a) impregnating a mesoporous material with an active pharmaceutical agent and a polyacrylate to produce an admixture;

b) adding a monomer to the admixture; and c) polymerizing the admixture to form a bone cement.

In another or a preferred aspect, the method further comprises a step of vacuum drying. Preferably, the vacuum drying is at room temperature.

In another or a preferred aspect, the method further comprises a step of shaping the bone cement in a mold.

In another or a preferred aspect, the method further comprises a step of adding a polymerization activator. Preferably, the polymerization activator is added at about the same time as the monomer. More preferably, before addition to the admixture, the polymerization activator is mixed with the monomer. Still more preferably, before addition to the admixture, the polymerization activator is in a liquid solution. Yet still more preferably, the polymerization activator is N,N-dimethyl-p-toludine.

In another aspect, the monomer is an acrylate monomer. More preferably, the monomer is methyl methacrylate.

In another aspect, the present invention provides a bone cement made by any of any of the methods described herein.

The present invention provides a method for preventing postoperative osteomyelitis, the method comprising the step of using the bone cement of the present invention.

This invention uses mesoporous silica nanoparticles ("MSN") and other nanostructured materials to formulate a PMMA-based bone cement for achieving an enhanced and controlled elution of antibiotics as well as pain-relief drugs. This invention makes a breakthrough to the limitation of low antibiotic release from commercial PMMA-based bone cements. Advantageously, the formulations enable a sustained release of antibiotics from the bone cement over a period of 80 days and achieves 70% of total drug release, whereas the commercial antibiotic bone cement (SmartSet GHV) only releases approximately 5% of antibiotics on the first day and almost negligible drug release thereafter. In addition, the mechanical properties such as compression strength and bending modulus of the formulated bone cements of the present invention remain equivalent to commercial PMMA-based bone cements. The present formulated bone cements exhibit good antibacterial properties and has low cytotoxicity to mouse fibroblast cells. The present invention is advantageous over currently available bone cements and prevents or reduces postoperative osteomyelitis.

In another embodiment, the present invention provides use of a bone cement, the bone cement comprising: a polyacrylate; and an active pharmaceutical ingredient, wherein the active pharmaceutical ingredient is disposed within a mesoporous material in the manufacture of a medicament for treating, preventing or reducing postoperative osteomyelitis.

These and other aspects will become more apparent when read with the following detailed description and drawings which follow.

DETAILED DESCRIPTION OF THE INVENTION

I. Introduction

Figure 1:
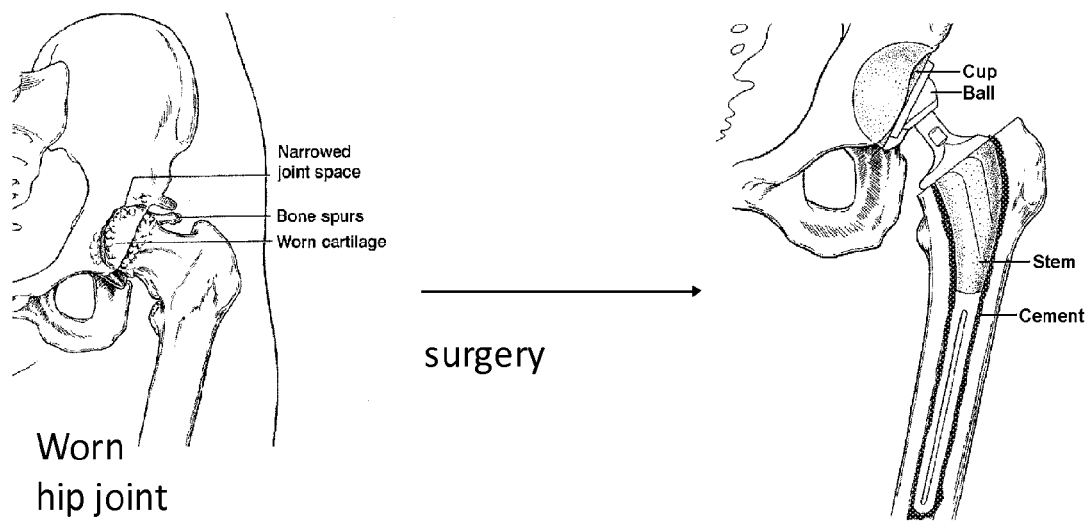
FIG. 1 is a diagram illustrating the use of exemplary cements according to some embodiments of the present invention.
Figure 2:
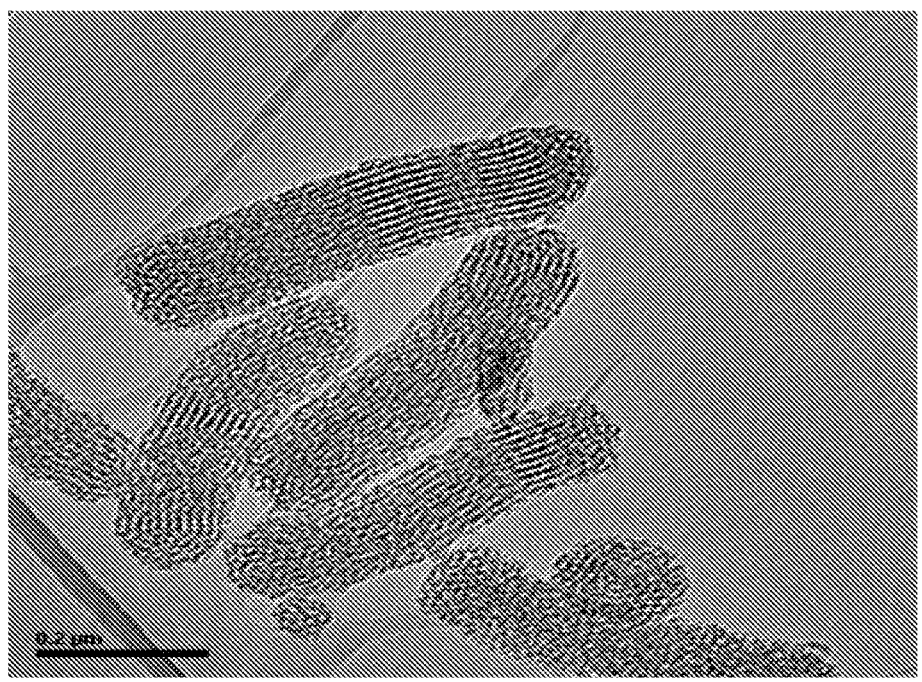
FIG. 2 is a diagram illustrating the release of drug encapsulated in mesoporous nanomaterials embedded in bone cement.

Arthroplasty (commonly referred to as hip and knee joint replacement) is currently the most common major orthopedic surgical procedure performed world-wide annually. Almost invariably for all these procedures, the prostheses are anchored to the contiguous bone using a poly(methyl methylacrylate)-based bone cement. Despite strict antiseptic operative procedures aimed at fighting infection, postoperative osteomyelitis remains a considerable problem in orthopedic surgery. The infection rates of joint replacement range from 1-3% after surgery operation. For patients with infection, total removal of the implant is often necessary and often leads to severe disability.

Several antibiotic-loaded bone cements are available, however, they are unable to sufficiently prevent postoperative osteomyelitis. The major problems plaguing all current antibiotic-polymer composites are their inadequate drug releasing kinetics. Since the active therapeutic agents can only be loaded into the composites by mechanical mixing or by adsorption directly into the polymer matrices, drug release at the implantation site is maintained for just a few days, which is shorter than is required to prevent infection. The drug is released by a sharp initial burst due to elution of antibiotics on surface of the bone cement, and not from the underlying sub-layers. The drug release is very limited in the later stage after a few days post-surgery. More than 90% of the loaded antibiotic may be retained within the PMMA matrix and never released into the surrounding tissue or medium. Therefore, the embedded antibiotic is unable to protect the surrounding tissue from infection.

In certain aspects of the present invention, mesoporous silica nanoparticles (MSN) are introduced to commercial bone cements, e.g., PMMA-based bone cements, to achieve a sustained release of antibiotics from the formulated bone cement. Sustained release of antibiotics can be used to protect surrounding tissues after surgery. Significant improvements over commercially available products overcome the low drug release limitation of commercial products and sustained release over a period of 80 days.

II. Definitions

As used herein, the following terms have the meaning ascribed to them unless specified otherwise.

The term "bone cement" includes a composite material consisting of a powdered polymer component and a liquid monomer component mixed together rapidly to form a viscous material with substantially no liquid phase. When the components are mixed together, a free radical polymerization occurs when the monomer becomes unstable by reacting with an initiator. Radicals bond with monomers, forming monomer radicals that can react with double bonds of the next monomer to propagate the polymer chain. Examples of commercially available bone cements useful in the present invention include, without limitation, polyacrylates, poly(methyl methacrylate, PMMA-based bone cement, methyl methacrylate copolymer and methyl methacrylate-styrene copolymer-based bone cements. Examples of methyl methacrylate copolymer-based bone cements include, but are not limited to, Simplex P (Stryker Orthopedics, Mahwah, N.J.) and SmartSet HV (DePuy Orthopedics Inc.; Warsaw, Ind.). In a preferred aspect, the inventive bone cement is a mesoporous material incorporated bone cement prepared via the processes described herein.

The term "mesoporous material" used herein includes nanoparticles or nanomaterials characterized by an average pore diameters of 2-50 nm, a high surface area (>900 m$^2$/g) and a uniformly arranged pore structure of hexagonal channels or cubic pores. Examples of mesoporous materials include, without limitation, mesoporous silica nanoparticles (MSN), alumina nanofibers, carbon nanotubes, titania nanotubes, hydroxyapatite nanorods, hydroxyapatite nanoparticles, and a combination thereof.

The terms "impregnated mesoporous material" or "incorporated mesoporous material" used herein include nanoparticles or nanomaterials that are loaded with active pharmaceutical agents, including, but not limited to, antibiotics and inflammatory drugs. The antibiotic-loaded nanomaterials can release the loaded pharmaceutical agent to the surrounding material and tissue. Examples of mesoporous materials include, without limitation, mesoporous silica nanoparticles, alumina nanofibers, carbon nanotubes, titania nanotubes, hydroxyapatite nanorods, hydroxyapatite nanoparticles, and a combination thereof. Methods for loading the mesoporous material with pharmaceutical agents may include wet impregnation, dry impregnation, or manual grinding of the mesoporous material and the therapeutic agent.

The term "polymerization initiator" includes a volatile catalytic chemical or radical that bonds to monomers, forming monomer radicals that can then attack the double bond of the next monomer and propagate the polymer chain. In a preferred embodiment of the present invention, the polymerization initiator is benzoyl peroxide. Alternatively or more preferably, the bone cement comprises about 0.8% to about 1.2% polymerization initiator by weight. Alternatively or still more preferably, a powder comprises the polymerization initiator The term "polymerization activator" or "polymerization accelerator" includes a chemical compound that reacts with the polymerization initiator to produce free radicals which are needed for the polymerization of the monomer component of bone cement. In a preferred embodiment, the polymerization activator is in a liquid solution of N,N-dimethyl-p-toludine. In a preferred embodiment, polymerization activator is added to the polymerization reaction at about the same time as the monomer.

The term "polyacrylate" as used herein includes polymers formed from a group of acrylate monomers. Examples of polyacrylate polymers include, but are not limited to, polymethylmethacrylates (PMMA) and/or a PMMA styrene copolymer, commercially available bone cements (e.g. PMMA-based bone cement powder), as well as commercially available bone cements further polymerized with monomers exemplified herein.

The term "compression strength" as used herein refers to the value calculated from obtained load-deformation curves derived from compression tests on cylindrical samples of bone cement 24+/−2 hours after forming and storage in dry air at 23° C. In some embodiments, the compression force is applied along the axis using a crosshead speed of 5 mm/min. The compression strength (CS) and the compression modulus ($E_2$) is calculated using the following equations:

$$CS = F/A,$$

$$E2 = \Delta\delta/\Delta\epsilon,$$

where F is the applied load (N) at the highest point of the load-deflection curve, A is the cross-section area of the sample tested. $\Delta\delta$ equals to $\Delta Fi/A$, where Fi is the applied load (N) at the point i of the straight-line portion of the trace, $\Delta\epsilon$ is $\Delta l_i/L$, where L is the length of the specimen and $l_i$ is the deflection corresponding to load Fi at a point in the straight-line portion of the trace.

The term "bending modulus" as used herein includes to a measure obtained from performing a multiple point bending test on beam specimens of bone cement 24+/−2 hours after forming and storage in dry air at 23° C. In some embodiments, the standard test method of ASTM D790-3 is utilized. For example, the span length is 20 mm and the loading rate is 1 mm/min. The bending modulus ($E_B$) was calculated according to the following equation:

$$E_B = L^3 m / 4bd^3,$$

where L is the support span (mm), b is width of beam tested (mm), d is depth of beam tested (mm), and m is slope of the tangent to the initial straight-line portion of load-deflection curve (N/mm)

The term "detectable sustained release" or "efficacious sustained release" includes to the maintained release of active pharmaceutical ingredient for a specified number of days (i.e., at least 15 days, preferably for at least 30, 50, 75, or 80 days). In another preferred, at least 10%, preferably at least 15%, 20%, 25%, 30%, 35%, 40%, 45%, 50%, 55%, 60%, 65%, 70%, 75% or 80% of the active pharmaceutical ingredient is released from the bone cement within 80 days.

The term "postoperative osteomyelitis" includes, but is not limited to, local or generalized infection of bone and bone marrow typically caused by bacteria introduced from trauma, surgery, use of implant, direct colonization from a proximal infection, or through systemic circulation.

Examples of active pharmaceutical ingredients include antibiotics and anti-inflammatory drugs. Antibiotics refer to a group of agents, but are not limited to, aminoglycoside antibiotics, glycopeptide antibiotics, macrolide antibiotics, and combinations thereof. Exemplary antibiotics may be active against gram-negative bacteria, as well as, active against both gram-positive and gram negative bacteria. Examples of the antibiotic include erythromycin, garamycin, gentamicin, kanamycin, neomycin, netilmicin, paramomycin, tobramycin, vancomycin, and their analogs, and a combination thereof.

Non-limiting examples of an analgesic or an anti-inflammatory drugs include steroid agents (e.g., substances related to cortisone, like methyprednisolone acetate) and non-steroidal agents (e.g., acetylsalicyclic acid, acetaminophen, celecoxib, refecoxib, ibuprofen and indomethacin).

In an alternative preferred embodiment, the active pharmaceutical agent is a combination of at least two compounds selected from the groups of antibiotics and anti-inflammatory agents as described herein.

In an preferred embodiment, the bone cement is comprised of a material that is opaque to X-rays and acts as a radiopacifier. Examples of X-ray contrast medium include, but are not limited to, zirconium dioxide, barium sulfate, or a combination thereof.

III. Description of the Embodiments

The present invention provides compositions for the preparation of bone cement formulated with drug releasing mesoporous nanomaterial (e.g., mesoporous incorporated bone cement). The present invention includes methods of impregnating mesoporous nanomaterial with active pharmaceutical ingredients. The present invention also provides methods of embedding or incorporating the impregnated mesoporous material into current commercially available bone cement. In particular embodiments, the compositions and methods of the present invention advantageously prevent or reduce postoperative osteomyelitis.

In one embodiment, the invention provides the compositions and methods of making a drug releasing bone cement. The bone cement comprises a polyacrylate; and one or a plurality active pharmaceutical ingredients; wherein the active pharmaceutical ingredient or plurality of ingredients is disposed within the a mesoporous material.

In one embodiment, the present invention provides a bone cement, the bone cement comprising:
 a polyacrylate; and
 an active pharmaceutical ingredient, wherein the active pharmaceutical ingredient is disposed within a mesoporous material.

In one aspect, the polyacrylate comprises polymerized methyl methacrylate. Preferably, the polyacrylate is poly(methyl methacrylate). Alternatively, or more preferably, the polyacrylate is in the form of a powder. In certain aspects, the polyacrylate is a commercially available bone cement (e.g., commercial PMMA-based bone cement) that has been further optionally polymerized with a monomer such as an acrylate monomer (e.g., methyl methacrylate).

In a preferred aspect, the mesoporous material is selected from the group consisting of mesoporous silica, alumina nanofibers, carbon nanotubes, titania nanotubes, hydroxyapatite nanorods, hydroxyapatite nanoparticles, and a combination thereof. Preferably, the mesoporous material is mesoporous silica. More preferably, the mesoporous silica has a particle size of about 0.1 μm to about 100 μm. Still more preferably, the mesoporous silica has a particle size of about 0.1 μm to about 10 μm. Yet still more preferably, the mesoporous silica has a particle size of about 0.1 μm to about 1 μm, such as 0.1 μm, 0.2 μm, 0.3 μm, 0.4 μm, 0.5 μm, 0.6 μm, 0.7 μm, 0.8 μm, 0.9 μm or 1 μm.

In an alternative aspect, the mesoporous silica comprises mesoporous silica nanoparticles. Still more preferably, the mesoporous silica is mesoporous silica nanoparticles.

In another preferred aspect, the active pharmaceutical ingredient is an antibiotic. Preferably, the antibiotic is selected from the group consisting of an aminoglycoside antibiotic, a glycopeptide antibiotic, a macrolide antibiotic, and a combination thereof. More preferably, the antibiotic is selected from the group consisting of erythromycin, gentamicin, tobramycin, vancomycin, and a combination thereof. Still more preferably, the antibiotic is gentamicin.

In an alternative preferred aspect, the antibiotic is a combination of at least two compounds selected from the group of erythromycin, gentamicin, tobramycin, and vancomycin. More preferably, the antibiotic is a combination of gentamicin and vancomycin.

In still another preferred aspect, the bone cement additionally comprises an analgesic or an anti-inflammatory. Preferably, the anti-inflammatory is a non-steroidal anti-inflammatory. More preferably, the non-steroidal anti-inflammatory is selected from the group consisting of ibuprofen and indomethacin.

In yet another aspect, the bone cement is about 1% to about 50% mesoporous material by weight. More preferably, the bone cement is about 1% to about 30% mesoporous material by weight. Still more preferably, the bone cement is about 1% to about 20% mesoporous material by weight, or about 4% to about 15% by weight, or from about 5% to about 12%, or even about 6% to about 10% by weight. In certain aspects, the inventive bone cement is at least 2% mesoporous material by weight. More preferably, the bone cement is from about 3% to about 30% mesoporous material by weight. Still more preferably, the bone cement is from about 1% to about 20%, such as 1%, 2%, 3%, 4%, 5%, 6%, 7%, 8%, 9%, 10%, 11%, 12%, 13%, 14%, 15%, 16%, 17%, 18%, 19% or 20% mesoporous material by weight.

In certain aspects, the bone cement is about 0.1%-30% active pharmaceutical agent by weight. In other aspects, the bone cement is about 1% to about 20% active pharmaceutical agent by weight or about 1% to about 10%, or even 1% to about 7% by weight. In other preferred aspects, the bone cement is at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, or 15% active pharmaceutical agent by weight. Preferably, the bone cement is at least 2% active pharmaceutical agent by weight. More preferably, the bone cement is at least 4% active pharmaceutical agent. Still more preferably, the bone cement is at least 6% active pharmaceutical agent.

In another preferred aspect, the bone cement is from about 1.3% to about 7% active pharmaceutical agent by weight, or about 2% to about 7% active pharmaceutical agent by weight. Still more preferably, the bone cement is from about 2% to about 4.5% or about 2.7% active pharmaceutical agent by weight. Alternatively, the bone cement is about 4.1% active pharmaceutical agent by weight, thus about 1%, 2%, 3%, 4%, 5%, 6%, or 7% and all fractions in between.

In an alternative aspect, the bone cement is from about 4.5% to about 7% active pharmaceutical agent by weight. Still more preferably, the bone cement is about 5.4% active pharmaceutical agent by weight.

In yet still another preferred aspect, the bone cement optionally comprises a material that is opaque to X-rays. Preferably, the material opaque to X-rays is selected from the group consisting of zirconium dioxide, barium sulfate, or a combination thereof. Alternatively or more preferably, the bone cement comprises about 10% to about 15%, such as 10%, 11%, 12%, 13%, 14%, or 15% of the opaque material by weight. Alternatively or still more preferably, the opaque material is a powder.

In still another preferred aspect, compression strength of the bone cement is at least 70%-95%, such as 70%, 75%, 80%, 85%, or 90% as high as compression strength of a control bone cement without the mesoporous material. Preferably, the compression strength of the bone cement is at least 80% as high as compression strength of a control bone cement without the mesoporous material. More preferably, the compression strength is at least 85% as high as the compression strength of the control bone cement without the mesoporous material. Still more preferably, the compression strength is at least 90% as high as the compression strength of the control bone cement without the mesoporous material. Yet still more preferably, the compression strength is at least 95% as high as the compression strength of the control bone cement without the mesoporous material. Preferably, the compression strength is at least as high as 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% as the compression strength of a control bone cement without the mesoporous material or even higher.

In yet still another preferred aspect, bending modulus of the bone cement is at least 80%-95% as high such as 80%, 81%, 82%, 83%, 84%, 85%, 86%, 87%, 88%, 89%, 90%, 91%, 92%, 93%, 94%, or 95% as high as bending modulus of a control bone cement without the mesoporous material. Preferably, the bending modulus is at least 85% as high as the bending modulus of the control bone cement without the mesoporous material. More preferably, the bending modulus is at least 90% as high as the bending modulus of the control bone cement without the mesoporous material. Still more preferably, the bending modulus is at least 95% as high as the bending modulus of the control bone cement without the mesoporous material. Yet still more preferably, the bending modulus is at least as high as the bending modulus of the control bone cement without the mesoporous material.

In another preferred aspect, detectible sustained release of the active pharmaceutical ingredient is maintained for at least 15 days to about 75 days, such as 15, 20, 25, 30, 35, 40, 45, 50, 55, 60, 65, 70, or 75 days. Preferably, detectible sustained release of the active pharmaceutical ingredient is maintained for at least 30 days. More preferably, detectible sustained release of the active pharmaceutical ingredient is maintained for at least 50 days. Still more preferably, detectable sustained release of the active pharmaceutical ingredient is maintained for at least 75 days.

In still another preferred aspect, efficacious sustained release of the active pharmaceutical ingredient is maintained for at least 15 days. Preferably, efficacious sustained release of the active pharmaceutical ingredient is maintained for at least 30 days. More preferably, efficacious sustained release of the active pharmaceutical ingredient is maintained for at least 50 days. Still more preferably, efficacious sustained release of the active pharmaceutical ingredient is maintained for at least 75 days such as for at least 15, 20, 25, 30, 35, 40, 45, 50, 55, 60, 65, 60, 65, or 70 days.

In yet still another preferred aspect, at least 10% to about 70%, such as 10, 15, 20, 25, 30, 35, 40, 45, 50, 55, 60, 65, or 70% of the active pharmaceutical ingredient is released from the bone cement within 80 days. Preferably, at least 15% of the active pharmaceutical ingredient is released from the bone cement within 80 days. More preferably, at least 20% of the active pharmaceutical ingredient is released from the bone cement within 80 days. Still more preferably, at least 25% of the active pharmaceutical ingredient is released from the bone cement within 80 days. Yet still more preferably, at least 30% of the active pharmaceutical ingredient is released from the bone cement within 80 days. Preferably, at least 35% of the active pharmaceutical ingredient is released from the bone cement within 80 days. More preferably, at least 40% of the active pharmaceutical ingredient is released from the bone cement within 80 days. Still more preferably, at least 45% of the active pharmaceutical ingredient is released from the bone cement within 80 days. Yet still more preferably, at least 50% of the active pharmaceutical ingredient is released from the bone cement within 80 days. Preferably, at least 55% of the active pharmaceutical ingredient is released from the bone cement within 80 days. More preferably, at least 60% of the active pharmaceutical ingredient is released from the bone cement within 80 days. Still more preferably, at least 65% of the active pharmaceutical ingredient is released from the bone cement within 80 days. Yet still more preferably, at least 70% of the active pharmaceutical ingredient is released from the bone cement within 80 days.

A. Methods of Preparation

In a preferred aspect, the present invention provides a method for preparing MSN formulated bone cement having a efficacious sustained release of an active drug, the method comprising:

a) impregnating a mesoporous material with one or a plurality of an active pharmaceutical agents to produce an impregnated mesoporous material;

b) mixing the impregnated mesoporous material with polyacrylate to produce an admixture;

c) adding a monomer to the admixture; and d) polymerizing the admixture to form the bone cement.

Figure 4:
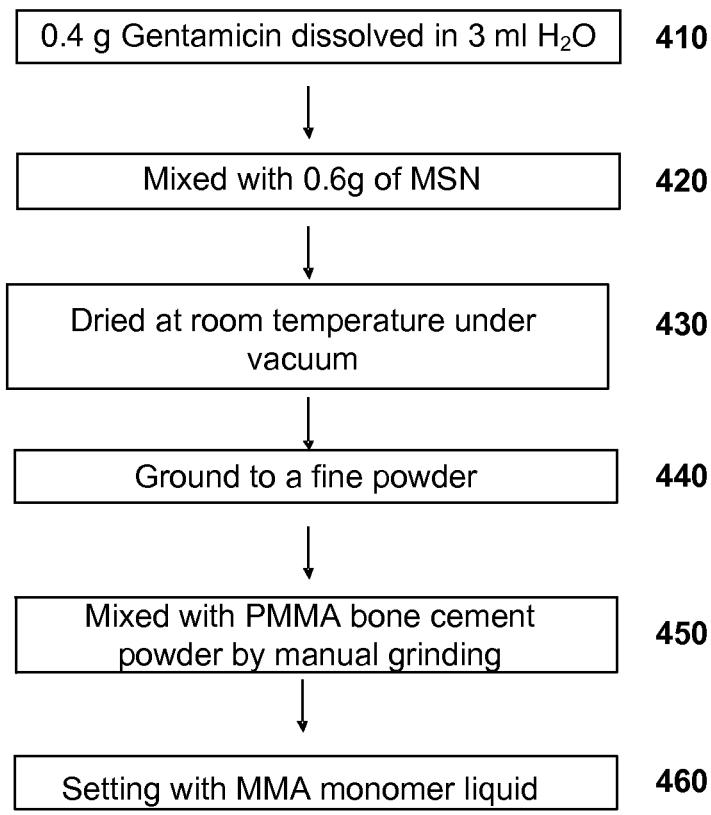
FIG. 4 shows a flow diagram illustrating an exemplary method 400 of preparation of drug releasing bone cements according to the present invention.

FIG. 4 is a flow diagram illustrates method of preparation 400 of exemplary bone cements according to embodiments of the present invention.

In a preferred embodiment, 0.4 g of gentamicin powder is dissolved 3 ml of water at step 410. At step 420 the dissolved gentamicin is mixed with 0.6 g of MSN. At step 430 the wet mixture is dried under vacuum at room temperature. At step

440 the dried powder is ground into a fine powder. PMMA bone cement powder (i.e., polyacrylate) is added and mixed by manual grinding. After mixing at step 450, MMA monomer liquor is added to the admixture and stirred thoroughly until the powder is fully wetted at step 460. The viscous bone cement is inserted into a mold and set overnight at room temperature.

In certain aspects, the step of mixing the mesoporous material with the polyacrylate comprises mixing a solid comprising the mesoporous material and a second solid comprising the polyacrylate.

In another aspect, the step of mixing the mesoporous material with the polyacrylate comprises dispersing the impregnated mesoporous material and the polyacrylate in a suspension.

In an alternative aspect, the method for preparing a MSN formulated bone cement having detectable sustained release of active pharmaceutical agents comprises:

(a) impregnating a mesoporous material with one or a plurality of active pharmaceutical agents and a polyacrylate to produce an admixture;

(b) adding a monomer to the admixture; and (c) polymerizing the admixture to form the bone cement.

Figure 5:
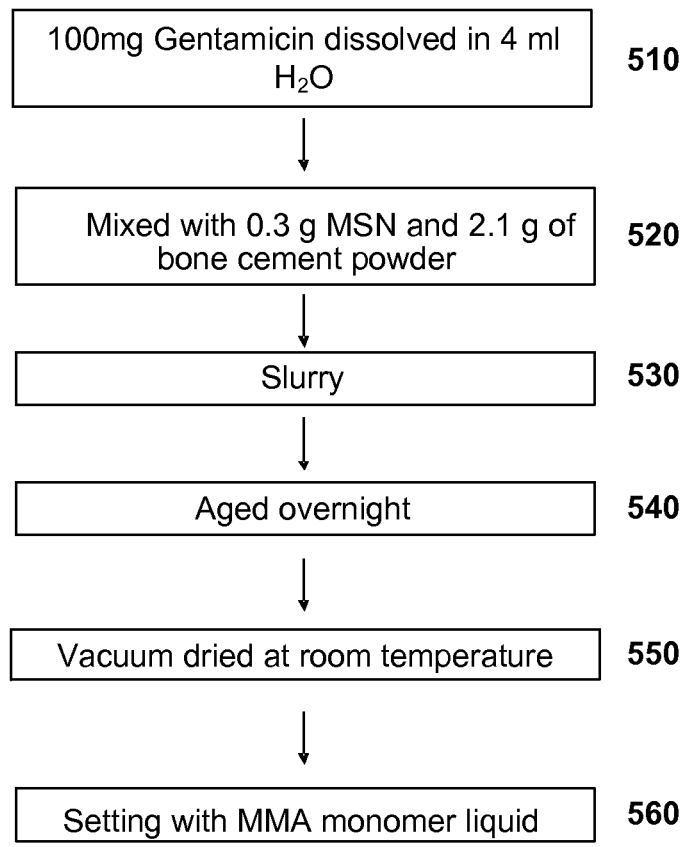
FIG. 5 shows a flow diagram illustrating another exemplary method 500 of preparation of drug releasing bone cements according to the present invention.

FIG. 5 is a flow diagram illustrates method of preparation 500 of exemplary bone cements according to embodiments of the present invention.

In another preferred embodiment, 100 mg of gentamicin powder is dissolved 4 ml of water at step 510. At step 520 the dissolved gentamicin is mixed with 0.3 g of MSN and 2.1 g of PMMA-based bone cement powder (i.e., polyacrylate). At step 530 the mixture is stirred thoroughly to produce an admixture with the consistency of a slurry. The admixture is aged overnight at room temperature at step 540. Next, at step 550 the admixture is dried at room temperature in a vacuum oven or dryer. MMA monomer liquor is added to the dried admixture and stirred thoroughly until the powder is fully wetted 560. The viscous bone cement is inserted into a mold and set overnight at room temperature.

In an exemplary embodiment, the bone cement is formulated to possess mechanical properties to match the bone in which it will be implanted. In certain embodiments, the cement is formulated to match the mechanical properties of commercially available bone cements without antibiotics.

In another or a preferred aspect of the second or third embodiment, the method further comprises a step of vacuum drying. Preferably, the vacuum drying is at room temperature.

In another or a preferred aspect of the second or third embodiment, the method further comprises a step of shaping the bone cement in a mold.

In another or a preferred aspect, the methods further comprise a step of adding a polymerization activator. Preferably, the polymerization activator is added at about the same time as the monomer. More preferably, before addition to the admixture, the polymerization activator is mixed with the monomer. Still more preferably, before addition to the admixture, the polymerization activator is in a liquid solution. Yet still more preferably, the polymerization activator is N,N-dimethyl-p-toludine.

In still another preferred aspect, the bone cement is prepared using a method described herein with polymerization initiator. Preferably, the polymerization initiator is benzoyl peroxide.

Alternatively or more preferably, the bone cement is prepared using about 0.8% to about 1.2% polymerization initiator by weight, such as 0.8%, 0.9%, 1.0%, 1.1% or, 1.2%. Alternatively or still more preferably, the polymerization initiator is a powder.

In another preferred aspect, the bone cement is prepared using a method described herein which uses a polymerization activator. Preferably, the polymerization activator is N,N-dimethyl-p-toludine. Alternatively or more preferably, the method used to prepare the bone cement herein uses about 1% to about 4%, such as 1%, 2%, 3%, or 4% of the polymerization activator by weight. Still more preferably, the method used to prepare the bone cement comprises about 2.5% of the polymerization activator by weight. Alternatively or yet still more preferably, the polymerization activator is a liquid.

In another or a preferred aspect, the monomer is an acrylate monomer. More preferably, the monomer is methyl methacrylate.

In another aspect, the present invention provides a bone cement made by any of any of the methods described herein.

B. Bone Cement Applications

In certain aspects, the drug releasing mesoporous incorporated bone cement of the present invention can be used in the augmentation of the bone-crew and bone-implant interface during joint replacement surgery. In addition, it is useful as a bone filler in areas of the body where bone may be deficient. Examples of such instances of deficiency include post-trauma with segmental bone loss, post-bone tumor surgery where excision of bone has occurred, and after total joint arthroplasty. The present invention may further be useful as a cement to hold and/or fix artificial joint components in bones of patients undergoing joint arthroplasty. As a non-limiting example, the present invention can be used as a strut to stabilize the anterior column of the spine after excision surgery. As a further example, the composite bone cement can serve as a bone graft substitute in spinal fusion procedures.

In one embodiment, the present invention is applied to the bone site to fill the site in a preferably space-filling manner, producing a secure fit between the bone and the implant. In a non-limiting example of bone reconstruction and repair, the bone cement is applied to the bone surface and pressed into or onto the site to force the cement into any surface irregularities, such as cracks, pits, pockets or holes.

In another preferred embodiment, the present invention is applied to the outer surface of the prosthesis stem and/or to the inner surface of the bone cavity. The stem is forced into the cavity until the prosthesis is fully seated and the bone cement is forced substantially and/or completely into the space between the stem and the bone.

Another aspect of the invention includes a method of making orthopedic or dental implants for the delivery of therapeutic agents and/or diagnostic agents into a cavity of the body of a patient. The certain embodiments, the present invention may be in the form of a curable matrix that can be implanted in a cavity in a body whereby the curable matrix takes on the shape of the cavity and forms a molded curable matrix. In certain embodiments, the curable matrix is a bone cement or a dental composite.

In certain embodiments, the invention provides a method for preventing or reducing postoperative osteomyelitis, the method comprising the step of using the bone cement of any of the aspects, preferred aspects, or combinations of preferred aspects of the first embodiment.

This invention uses mesoporous silica nanoparticles and other nanostructured materials to formulate a PMMA-based bone cement for achieving an enhanced and controlled elution of antibiotics as well as pain-relief drugs. This invention makes a breakthrough to the limitation of low antibiotic release from commercial PMMA-based bone cements. The inventive formulations enables a sustained release of antibiotics from the bone cement over a period of 80 days and achieves 70% of total drug release, whereas the commercial antibiotic bone cement (SmartSet GHV) only releases approximately 5% of antibiotics on the first day and almost negligible drug release thereafter. In addition, the mechanical properties such as compression strength and bending modulus of the formulated bone cements in the present invention remain equivalent to commercial PMMA-based bone cements. The newly formulated bone cements exhibit good antibacterial properties and has low cytotoxicity to mouse fibroblast cells. The present invention is advantageous over currently available bone cements and has high potential for preventing postoperative osteomyelitis.

Although the present invention is preferably for mammals such as human beings, a skilled artisan will appreciate that the present invention is applicable for veterinary and laboratory uses.

IV. Examples

Example 1

Preparation of Mesoporous Silica Nanoparticles

Mesoporous silica nanoparticles (MSN) were prepared using fluorocarbon-surfactant-mediated synthesized procedure (see U.S. patent application Ser. No. 11/631,342; Gao et al., *J. Phys. Chem. B*, 113:1796-1804 (2010); Han Y and Ying J Y., *Angew. Chew. Int. Ed.*, 44:288-92 (2005)). Typically, 0.5 g of Pluronic P123 (triblock polymer) and 1.4 g of FC-4 (fluorocarbon surfactant) were dissolved in 80 ml of HCl solution (0.02 M), followed by the introduction of 2.0 g of tetraethoxysilane under stirring. The solution was continuously stirred at 30° C. for 24 h and then transferred into a polypropylene bottle and kept at 100° C. for 1 day. The resultant solid was recovered by centrifuging and washed with deionized water twice, and then dried at 55° C. for 12 h. To remove the template molecules, the material was heated from room temperature to 550° C. at a heating rate of 2° C./min and followed by calcination (thermal decomposition) in air for 6 h.

Example 2

Preparation of Mesoporous Material Incorporated Antibiotic Bone Cements by Method 400

This example illustrates a method for impregnating one or a plurality of antibiotics in MSN and embedding antibiotic loaded nanoparticles into commercially available PMMA-based bone cement (see Table 1). Gentamicin was loaded onto MSN by wet impregnation. Typically, 0.40 g of gentamicin was dissolved in 3 ml deionized water. In one experiment, 0.60 g of MSN powder was impregnated with gentamicin solution under stirring and aged for 24 h. The mixture was dried under vacuum at room temperature under vacuum for 48 h. The dried gentamicin loaded MSN was ground to fine powder and a certain amount of gentamicin-MSN powder was mixed with commercial bone cement solid powder by manual grinding. The samples of antibiotic loaded bone cement were prepared by mixing the powder with the liquid monomer in a ratio of 2g/ml in a bowl in a laminar flow hood, in accordance with the manufacture's instruction. Monomer liquid was added to the polymer-MSN mixture in a bowl and was stirred using spatula until the powder was fully wetted. The soft mixture was inserted into the mold with dimension of 6 mm in diameter and 12 mm in height. The filled mold was pressed between two glass plates for harden overnight at room temperature. The hardened bone cement cylinders were pulled out of the mold and stored under sterile condition at room for in-vitro drug release test and compression test. Samples A-1~A-6 prepared by method-A are listed in Table 2.

TABLE 1

Composition of commercially available PMMA-based bone cements used in the present invention.

|  | Simplex P (w/w %) | Smartset HV (w/w %) | Smartset GHV (w/w %) |
|---|---|---|---|
| Powder |  |  |  |
| Methylmethacrylate methacrylate copolymer | 15.00 | 84.00 | 80.46 |
| Methyl methacrylate-styrene copolymer | 73.72 | — | — |
| Zirconium dioxide |  | 15.00 | 14.37 |
| Barium sulphate | 10.00 |  |  |
| Benzoyl peroxide | 1.28 | 1.00 | 0.96 |
| Gentamicin | — | — | 4.22 |
| Liquid |  |  |  |
| Methylmethacrylate | 97.49 | 97.50 | 97.50 |
| N,N-dimethyl-p-toludine | 2.50 | 2.50 | 2.50 |
| Hydroquinone | 0.0075 |  |  |

% by weight (w/w) of powder component and liquid component.

TABLE 2

MSN formulated composite bone cement prepared by Method 400.

|  | MSN wt % | Drug loading wt % | PMMA Powder (g) | Gentamicin-MSN (g) | MMA (ml) |
|---|---|---|---|---|---|
| Smartset-GHV* | 0 | 2.87 | 2.0 | 0 | 1.0 |
| A-1 | 0 | 3.40 | 1.90 | 0.10 g Gentamicin | 1.0 |
| A-2 | 2.04 | 1.36 | 1.90 | 0.10 | 1.0 |
| A-3 | 4.08 | 2.72 | 1.80 | 0.20 | 1.0 |
| A-4 | 6.12 | 4.08 | 1.70 | 0.30 | 1.0 |
| A-5 | 8.15 | 5.44 | 1.60 | 0.40 | 1.0 |
| A-6 | 10.19 | 6.79 | 1.50 | 0.50 | 1.0 |

*SMARTSET GHV is a commercial PMMA-based bone cement loaded with gentamicin (4.22 wt % in powder; Depuy Co.)

Figure 6:
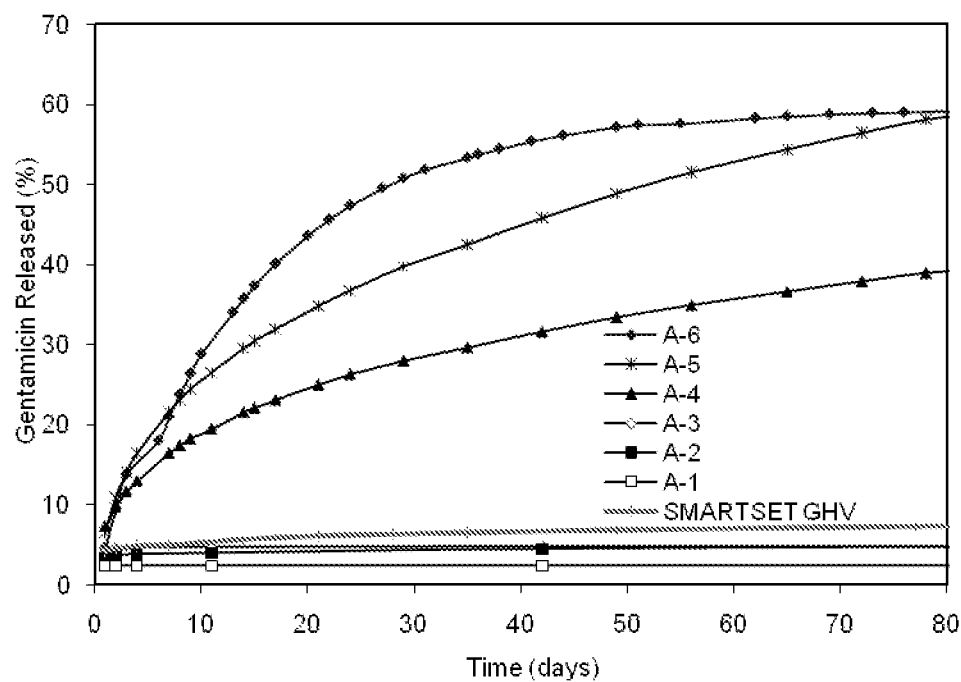
FIG. 6 is a graph of the drug release profiles of MSN formulated bone cement prepared with Simplex P according to a method of the present invention.

FIG. 6 illustrates that the commercial antibiotic bone cement (SmartSet GHV) exhibited very low drug release; only less than 7% of gentamicin was released over the period of 80 days. When gentamicin was directly mixed with PMMA of commercial Simplex-P bone cement (A-1), only about 3% of gentamicin released was observed on the first day of immersion in phosphate buffered saline (PBS) solution. No gentamicin release was detectable in the following 80 days of investigation. The drug release rate is obviously affected by the content of MSN in the final composition. For the samples A-2 and A-3 with MSN contents of 2.04 wt % and 4.08 wt % respectively, the release of gentamicin only reached 5% on the first day of immersion and there was no release subsequently. More than 90% of gentamicin was still retained inside the matrix of the bone cement. When the MSN content was increased to 6.12 wt % in the final composite, the release of gentamicin from the sample of A-4 is significantly enhanced. After 7.3% of the gentamcin was released on the first day, sustained release of gentamicin bone was observed over a period of 80 days. In total 40% of the gentamicin was eventually released. Further increasing the content of MSN to 8.15 wt % resulted in the sustained release of gentamicin to 58% in 80 days. When the MSN content was increased to 10.19 wt % (sample A-6), a faster release rate was detected in the early stages between 10-30 days compared to that of A-5. Eventually after a period of 80 days, a similar percentage of gentamicin was released. The antibiotic loaded bone cement described herein advantageously exhibits increased antibiotic release from commercial PMMA-based bone cements (e.g., SmartSet GHV) due to a diffusion network created by mesoporous silica nanoparticles.

Example 3
Preparation of Mesoporous Material Incorporated Antibiotic Bone Cements by Method 500

This example illustrates another method for impregnating one or a plurality of antibiotics in MSN and embedded the antibiotic loaded nanoparticles into commercially available PMMA-based bone cement. Gentamicin was loaded into bone cement powder by impregnation together with MSN. Typically, 0.30 g of MSN was dispersed in 4 ml of aqueous solution containing 0.10 g of gentamicin. Subsequently, 2.10 g of bone cement powder was immersed into the aqueous suspension to form slurry under stirring. The wet mixture was dried under vacuum at room temperature. The obtained mixture of gentamicin-MSN-PMMA was ground to fine powder. The samples of antibiotic loaded bone cement were prepared by mixing the powder with the liquid monomer in a ratio of 2 g/ml in a bowl in a laminar flow hood, in accordance with the manufacture's instruction. Monomer liquid was added to the polymer-MSN mixture in a bowl and was stirred using spatula until the powder was fully wetted. The soft mixture was inserted into the mold with dimension of 6 mm in diameter and 12 mm in height. The filled mold was pressed between two glass plates for harden overnight at room temperature. Samples prepared by this method are listed in Table 3 and denoted as B-1~B-5.

In another alternative method of preparing antibiotic loaded MSN formulated bone cement, a certain amount of gentamicin, MSN and bone cement powder are thoroughly mixed together by manual grinding before polymerization with monomer. In this example, 2.0 g of the mixed powder was mixed with 1.0 ml monomer liquid, in a bowl in a laminar flow hood, in accordance with the manufacture's instruction. Monomer liquid was added to the polymer-MSN mixture in a bowl and was stirred using spatula until the powder was fully wetted. The soft mixture was inserted into the mold with dimension of 6 mm in diameter and 12 mm in height. The filled mold was pressed between two glass plates for harden overnight at room temperature. The sample prepared by this method is denoted as C-1 and listed in Table 3.

TABLE 3

MSN formulated bone cement prepared by the method above.

| | Simplex-P Powder (g) | MSN (mg) | GTMC (mg) | MMA (ml) | MSN % | Drug % |
|---|---|---|---|---|---|---|
| B-1 | 1.68 | 0.24 | 80 | 1.0 | 8.15 | 2.72 |
| B-2 | 1.76 | 0.16 | 80 | 1.0 | 5.44 | 2.72 |
| B-3 | 1.84 | 0.08 | 80 | 1.0 | 2.72 | 2.72 |
| B-4 | 1.68 | 0.24 (SM) | 80 | 1.0 | 8.15 | 2.72 |
| B-5 | 1.68 | 0.24 (micro) | 80 | 1.0 | 8.15 | 2.72 |
| C-1 | 1.68 | 0.24 | 80 | 1.0 | 8.15 | 2.72 |

Example 4
Mesoporous Material Incorporated Antibiotic Bone Cements for Sustained Drug Release This example illustrates a method for impregnating one or a plurality of antibiotics in MSN and embedding antibiotic loaded nanoparticles into commercially available PMMA-based bone cement. In this example, GTMC was loaded bone cement powder by impregnation together with MSN. Typically, 0.24 g of MSN was dispersed in 4 ml of aqueous solution containing 0.080 g of gentamicin. Subsequently, 1.68 g of bone cement powder (i.e., was immersed into the aqueous suspension to form slurry under stirring. The wet mixture was dried under vacuum at room temperature. The obtained mixture of gentamicin-MSN-PMMA was ground to fine powder and 1 ml MMA monomer was used for setting. Samples prepared by this method are listed in Table 4A and denoted as B-1~B-3.

TABLE 4A

MSN formulated bone cement prepared by method above.

| | MSN wt % | Drug loading wt % | PMMA (g) | MSN (mg) | GTMC (mg) | MMA (ml) |
|---|---|---|---|---|---|---|
| Smartset GHV | | 2.87 | 2 | 0 | | 1.0 |
| B-1 | 8.15 | 2.72 | 1.68 | 0.24 | 80 | 1.0 |
| B-2 | 5.44 | 2.72 | 1.76 | 0.16 | 80 | 1.0 |
| B-3 | 2.72 | 2.72 | 1.84 | 0.08 | 80 | 1.0 |

TABLE 4B

MSN formulated bone cement compared to other antibiotic-loaded bone cements.

| Bone cements | Company | Gentamicin loaded (wt %) | Total Antibiotic Released (%) |
|---|---|---|---|
| SMARTSET GHV | Depuy Co | 4.2% in powder | ~5% |
| Palacos R + G | Zimmer | 2.5% in powder | ~10% |
| Simplex P | Stryker | Manually mixed with 5% to powder | ~3% |
| inventive | | Simplex P powder + MSN + gentamicin 4% in powder | ~70% Sustained release |

In Vitro Drug Release Study

The drug release study was conducted by socking two cylinder samples of each composition in 5 ml PBS buffer (pH 7.4). The sample was put in an incubator shaker operated at 37° C. and 40 rpm. The release medium was withdrawn at predetermined time intervals, and replaced with fresh PBS buffer (5 ml) each time. The accumulative amount of gentamicin released was calculated based on the initial weight of bone cement cylinder and the drug content. The gentamicin release was followed for 80 days.

An indirect method was used for measurement of gentamicin concentration by UV-vis spectrophotometer (Cary 50, Varian Co) because gentamicin does not absorb ultraviolet nor visible light. The o-phthaldialdehyde was used as a derivatizing agent to react with the amino groups of gentamicin and yield chromophoric products. The reaction was carried out making 1 ml of our problem gentamicin in solution react with 1 ml of isopropanol (to avoid the precipitation of the products formed) and 1 ml of o-phthaldialdehyde reagent. After fully mixed, the concentration of gentamicin sulfate was determined by the UV absorbance at 332 nm.

The concentration of ibuprofen, vancomycin and indomethacin was directly determined by UV-vis detection without the presence of reactive reagent.

In Vitro Cytotoxicity Assay

3T3 mouse fibroblasts cells (3T3-Swiss albino, ATCC) were cultured in a complete growth culture medium in a 5% $CO_2$ incubator. The complete growth culture medium was prepared with Dulbecco's Modified Eagle's Medium (DMEM) supplemented with 10% fetal bovine serum, 1 mm l-glutamine and penicillin (100 U/ml).

Cell viability testing was carried out via the reduction of the MTT reagent (3-[4,5-dimethyl-thiazol-2-yl]-2,5-diphenyltetrazolium bromide, Sigma). This assay provides a simple method for determining comparative cell viability using a standard microplate absorbance reader. The MTT assay was performed with the bone cement substrates placed at the bottom of a 96-well plate following the standard procedure with minor modifications. Control experiments were carried out using the complete growth culture medium only (serving as non-toxic control) and 1% Triton X-100 (Sigma) (as toxic control). 3T3 fibroblasts in the complete growth culture medium (100 μl) were seeded at a density of $10^4$ cells/well in a 5% $CO_2$ incubator for 24 h. The culture medium from each well was then removed and 100 μl of medium and 20 μl MTT solution (5 mg/ml in PBS) were then added to each well. After 4 h of incubation at 37° C. and 5% $CO_2$, the media were removed and the formazan crystals were solubilized with 100 μl dimethyl sulfoxide (DMSO, Sigma) for 15 min. The optical absorbance was then measured at 570 nm on a microplate reader (Tecan GENios). Six samples were tested for each type of bone cement.

Viability of Bacteria on Bone Cement Surface

The bone cement rectangular beams with dimension of 25×10×2 mm were immersed in SBF buffer for two weeks prior to antibacterial test. The viability of bacteria (*S. aureus*) on the surface of bone cements was investigated by staining with a combination dye (LIVE/DEAD Baclight bacteria viability kits, Molecular Probes, L13152). After immersion in the bacteria suspension of $10^8$ cells/ml in broth at 37° C. for 3 h, the substrates were washed with water and stained using 50 μl of the combination dye (propidium iodide (PI) and SYTO 9) and subsequently analyzed with a Leica DMLM microscope with a 100 W Hg lamp. The viable and non-viable cells can be distinguished under the fluorescence microscope since the viable cells appear green under the light microscope while non-viable or membrane compromised cells appear red.

Testing of Mechanical Property

Three point bending test was performed on the Instron universal materials testing machine (Model 5544). According to the standard test method of ASTM D790-3, the span length was 20 mm and loading rate was 1 mm/min. The bending modulus ($E_B$) was calculated according to the following equation:

$E_B = L^3 m / 4bd^3$, where L is the support span (mm), b is width of beam tested (mm), d is depth of beam tested (mm), and m is slop of the tangent to the initial straight-line portion of load-deflection curve (N/mm).

The compression tests were carried out on the bone cement cylinders with same dimension as that for drug release investigation. The compression force was applied along the axis using a crosshead speed of 5 mm/min. The compression strength was calculated from the obtained load-deformation curves. The compression strength (CS) and the compression modulus ($E_2$) were calculated using the following equations:

$CS = F/A$, $E2 = \Delta\delta/\Delta\epsilon$, where F is the applied load (N) at the highest point of the load-deflection curve, A is the cross-section area of the sample tested. $\Delta\delta$ equals to $\Delta Fi/A$, where Fi is the applied load (N) at the point i of the straight-line portion of the trace, $\Delta\epsilon$ is $\Delta l_i/L$, where L is the length of the specimen and $l_i$ is the deflection corresponding to load Fi at a point in the straight-line portion of the trace.

Results

Figure 7:
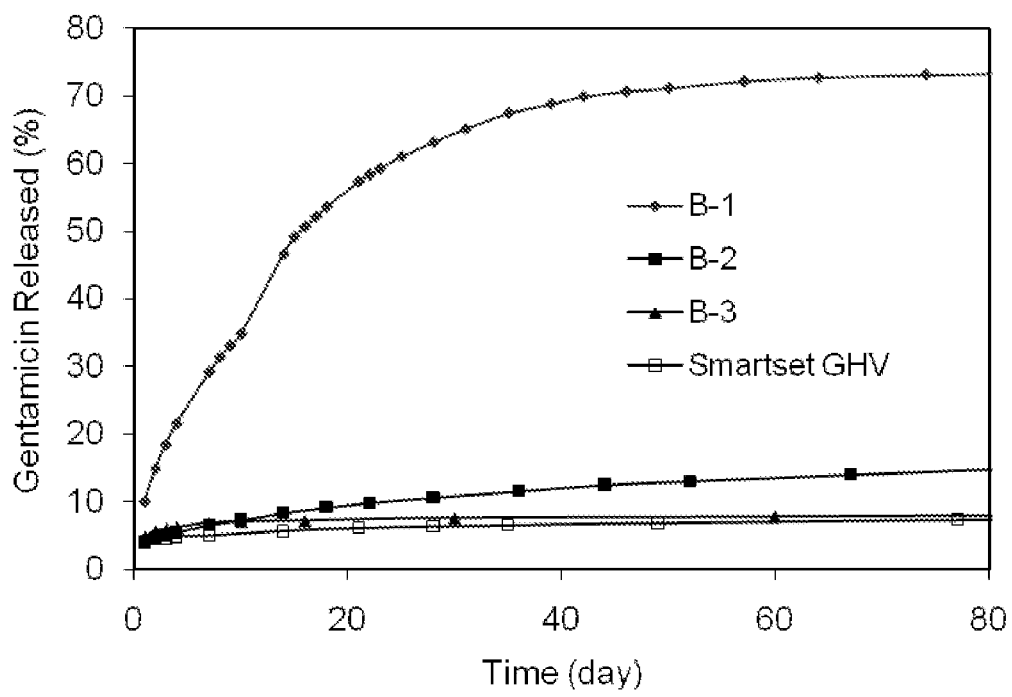
FIG. 7 is a graph of the drug release profiles of MSN formulated bone cement prepared with SmartSet HV according to a method of the present invention.

FIG. 7 displays the effect of MSN content on gentamicin release profiles of the formulated bone cement samples listed in Table 4A. The sample B-1 achieved more than 70% of gentamicin released over a period of 80 days, which is much higher than that released from the commercial antibiotic bone cement SmartSet GHV (see Table 4B). As comparison, the gentamicin release from sample B-2 is suppressed when the MSN content was reduced from 8.15 wt % to 5.44 wt %. Sample B-2 only showed 15% of gentamicin release in 80 days of immersion in PBS buffer. The sample B-3 did not exhibit an improvement on release of gentamicin although it contains 2.72 wt % of MSN in the formulation. Although sample B-1 has the same content of MSN as the sample A-5 in Table 2, sample B-1 showed a higher drug release rate than A-5.

Figure 8:
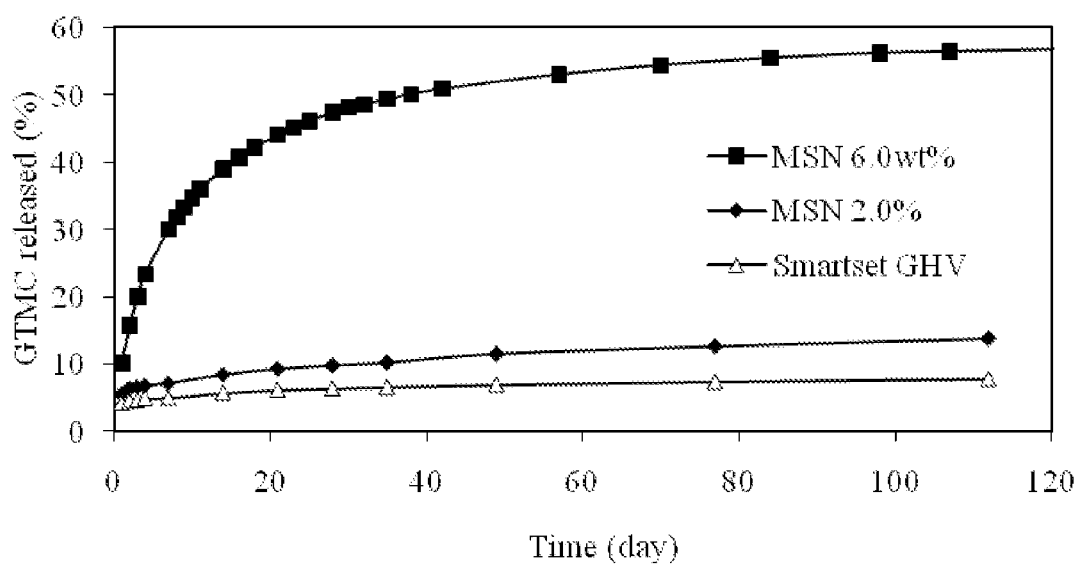
FIG. 8 is a graph of the drug release profiles of MSN formulated bone cement prepared with SmartSet HV.

In addition to using Simplex-P, another commercial bone cement with no antibiotic called Smartset HV is also formulated with MSN and gentamicin. As shown in FIG. 8, when the commercial bone cement of SmartSet HV was used, the gentamicin release was similarly affected by the content of MSN formulated in the composite bone cement. The composite bone cement exhibited more than 55% of gentamicin released when 6.0 wt % of MSN was introduced. When 2 wt % of MSN was incorporated, the drug release was much lower. In comparison, the commercial gentamicin-loaded SmartSet GHV bone cement showed only less than 7.0% of gentamicin released. Therefore, the drug release data of our formulations showed a significant advantage over commercially available bone cement products.

The MSN nanoparticles incorporated in the bone cement is believed to form a path network for gentamicin diffusion from the composite. As indicated in the FIG. 3, for gentamicin formulated bone cement in the absence of MSN nanoparticles, gentamicin became embedded inside the PMMA matrix during polymerization and could not diffuse to surface of bone cement for release. For the gentamicin-MSN loaded bone cement composite, antibiotic was stored inside the mesoporous channels of the rod-like MSN nanoparticles. A critical amount of MSN is required to establish the necessary network necessary for antibiotics to diffuse from the matrix and to be released into the surrounding medium. When the content of MSN is below 5 wt %, the gentamicin loaded MSN particles remained embedded in the bone cement matrix. However, once the MSN content is increased to 6 wt % or above, a diffusion network is built and gentamicin is able to diffuse from bone cement and be released to the medium.

Antibacterial Property

Figure 9:
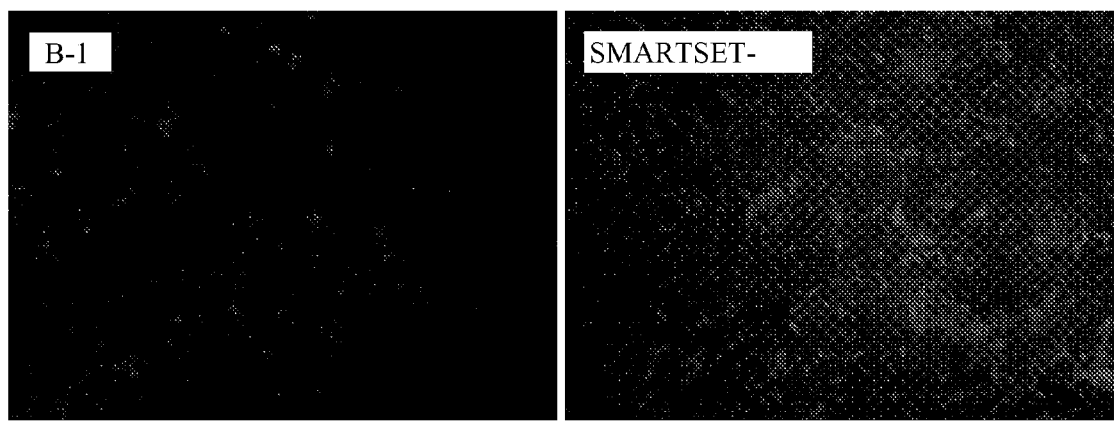
FIG. 9 is an image of viable and non-viable bacterial cells cultured on gentamicin loaded MSN bone cement and SmartSet GHV.

Before antibacterial testing, the sample was soaked in PBS solution for two weeks. The samples were then exposed to a bacteria containing solution for three hours. Under fluorescence microscope, the viable cells appear green and dead cells appear red. As seen in FIG. 9, the formulated composite bone cement B-1 exhibited a much better antibacterial property than the commercial antibiotic bone cement SmartSet GHV. The result is consistent with the sustained release of gentamicin from B-1 in PBS buffer.

Mechanical Properties

Figure 10:
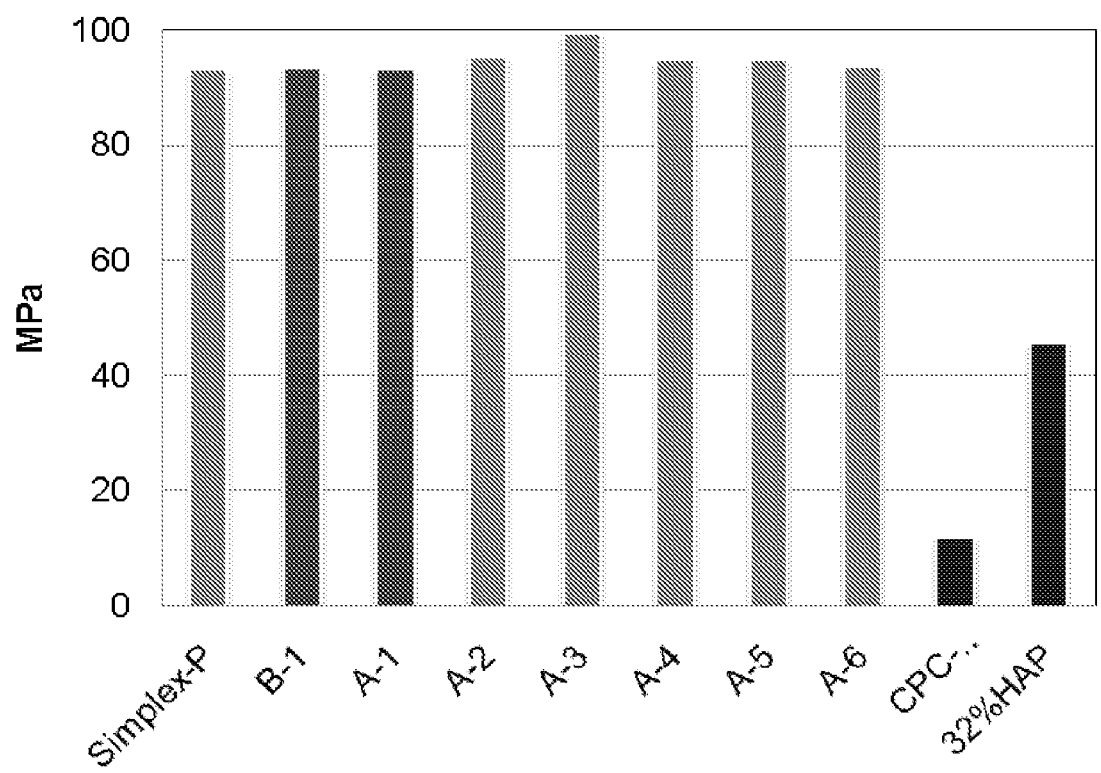
FIG. 10 illustrates the compression strengths of exemplary gentamicin loaded MSN bone cements composed according to the present invention.
Figure 11:
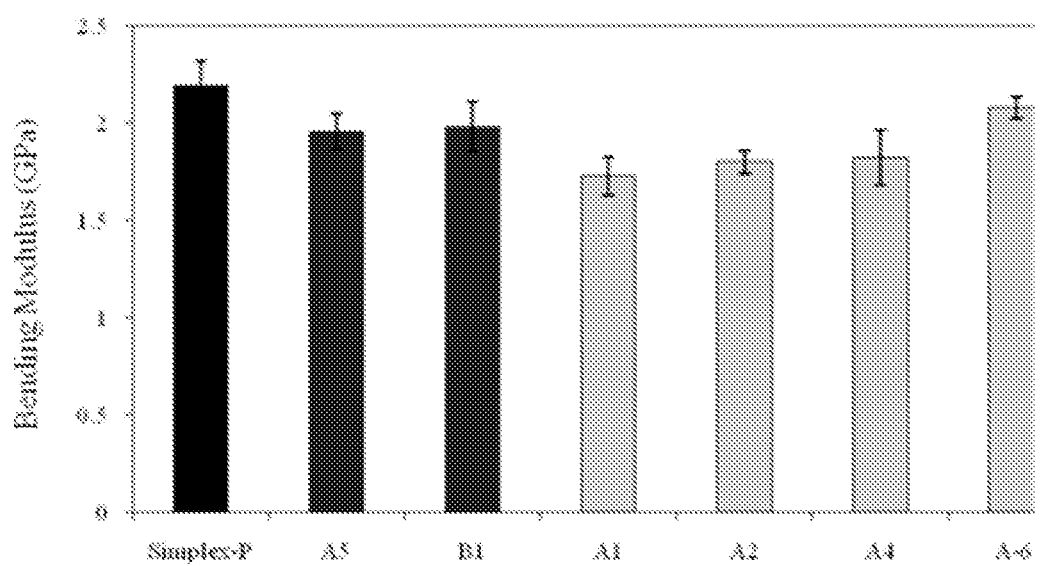
FIG. 11 shows the bending modulus of exemplary gentamicin loaded MSN bone cement composed according to the present invention.
Figure 12:
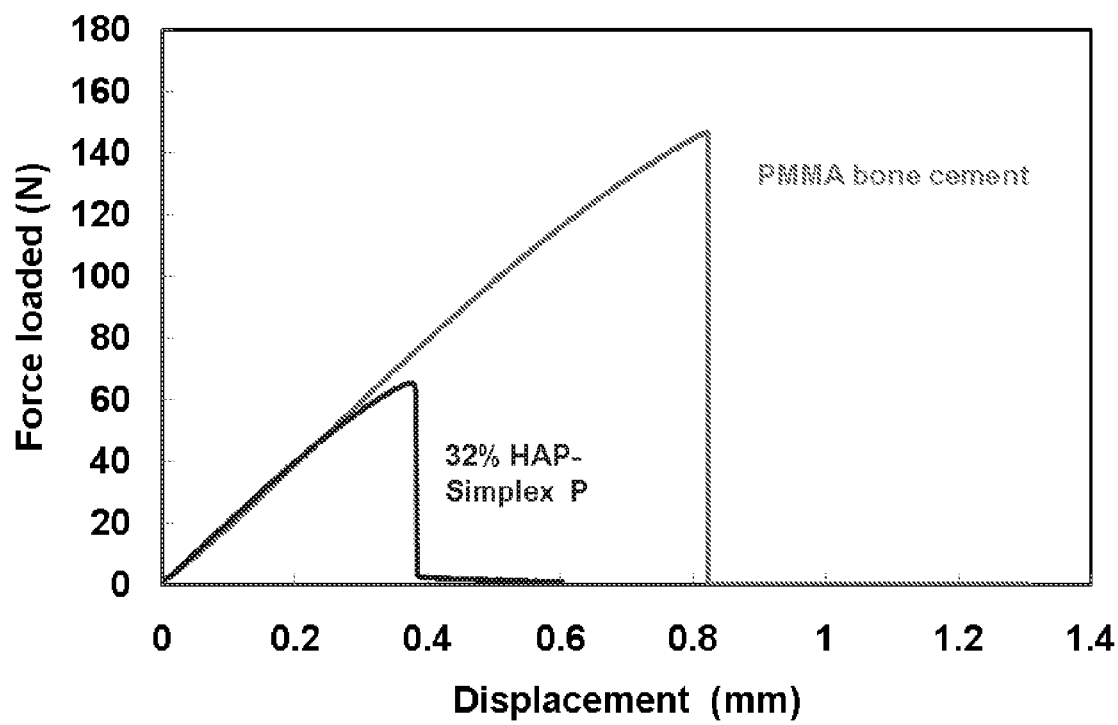
FIG. 12 shows the load-displacement curve for compression test of hypoxyapatite containing bone cement.

FIGS. 10 and 11 show that the mechanical properties of the present invention are well retained compared to other PMMA-based bone cements. It was reported that formulation of PMMA-based bone cement with 35 wt % of hypoxyapatite could improve drug release from antibiotic loaded bone cement (Padilla et al., *J. Control Release*, 83: 343-352 (2002)). In compression strength assays shown in FIG. 10, hypoxyapatite containing bone cement showed a 50% reduction of compression strength compared to bone cement alone. The compression strength of the present invention was comparable to commercially available bone cement (e.g., Simplex P). FIG. 12 illustrates the reduction of bending modulus in hypoaxyapatite containing bone cement compared to bone cement alone.

Cytotoxicity of Nanomaterials

Figure 18:
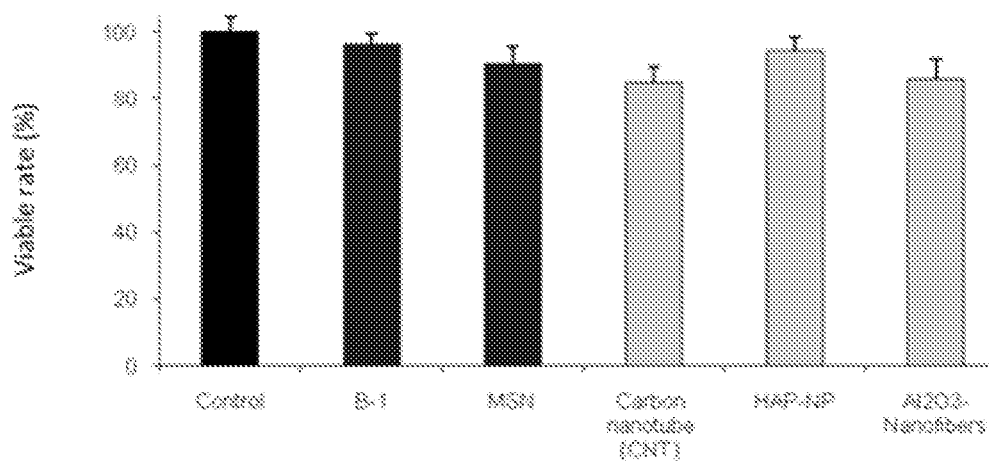
FIG. 18 shows the cytotoxicity of mesoporous nanomaterial functionalized bone cements.

Compared with a non-toxic control sample, MSN also showed low toxicity to the cells of mouse fibroblasts. As shown in FIG. 18, the sample B-1 with 12 wt % of MSN in PMMA exhibited very little toxicity as compared with the non-toxic control sample. The result indicated that MSN is safe for formulation with bone cement for drug delivery. In addition, several inert nanostructured materials are also suitable for application as bone cement fillers to control the drug release from antibiotic bone cements.

Conclusion

Figure 3:
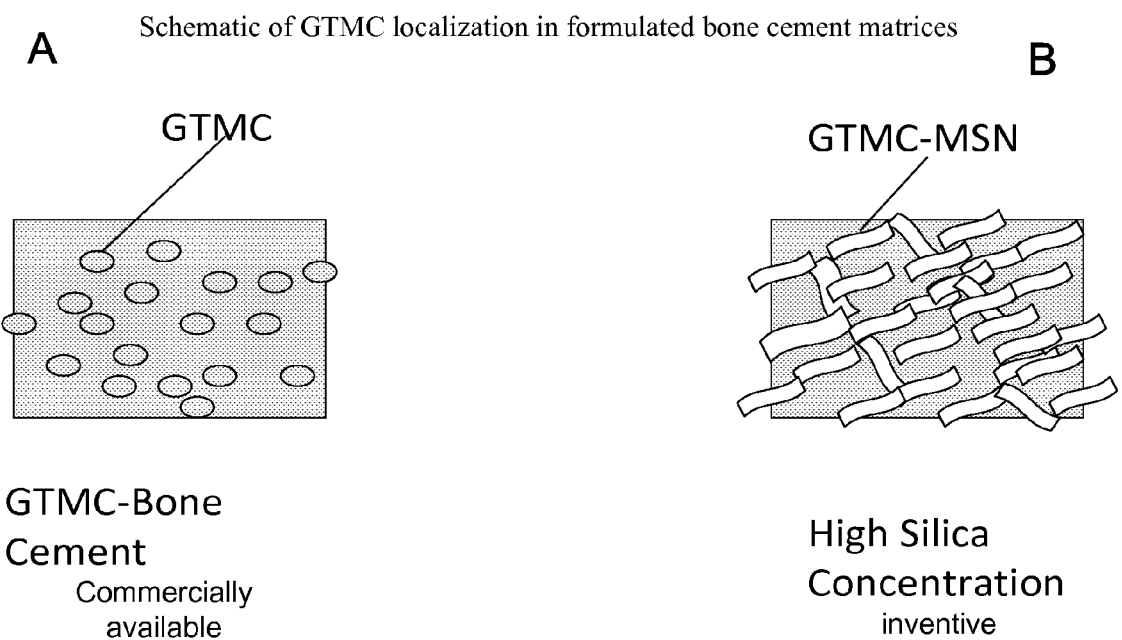
FIG. 3 is an image of (A) commercially available bone cement and (B) an inventive embodiment of mesoporous nanoparticles incorporated in bone cement.

As compared with commercial antibiotic loaded bone cements, this example demonstrates that the exemplary MSN formulated bone cement depicted in FIG. 3 achieves a breakthrough in the enhancement of drug release from the bone cement. Drug release profiles are improved by the MSN formulation which builds up an effective diffusion network. Mechanical properties are well retained for MSN formulated bone cement. In addition, antibacterial properties are improved by maintaining very low cytotoxicity in cultured cells. The novel formulation has high potential for commercial application in the prevention of postoperative ostomyelitis.

Example 5
Mesoporous Material Incorporated Bone Cement Containing a Plurality of Antibiotics The compositions and methods of the present invention can be applied for prepare MSN formulated bone cement consisting of a plurality of antibiotics. A typical protocol entails a impregnating and encapsulating a plurality of antibiotics in MSN and commercially available PMMA-based bone cement. As a non-limiting example, 0.10 g of gentamicin and 0.10 g of vancomycin was dissolved in 4 ml of water to form a mixed solution. 0.30 g of MSN powder was added to the mixed solution under stirring and MSN particles were dispersed homogeneously in the slurry. Then 2.0 g of PMMA bone cement powder was immersed into the aqueous suspension to form slurry by stirring. The wet mixture was dried under vacuum at room temperature. The obtained mixture of bi-antibiotics containing solid was ground to fine powder. The samples of bi-antibiotic loaded bone cement were prepared by mixing the powder with the liquid monomer in a ratio of 2 g/ml in a bowl in a laminar flow hood, in accordance with the manufacture's instruction. Monomer liquid was added to the polymer-MSN mixture in a bowl and was stirred using spatula until the powder was fully wetted. The soft mixture was inserted into the mold with dimension of 6 mm in diameter and 12 mm in height. The filled mold was pressed between two glass plates for harden overnight at room temperature. In addition two or more antibiotics can be formulated to bone cement. The antibiotics can be selected from a group consisting of, but not limited to, erythromycin, garamycin, gentamicin, kanamycin, neomycin, netilmicin, paramomycin, tobramycin, vancomycin, and their analogs, and combinations thereof.

Figure 13:
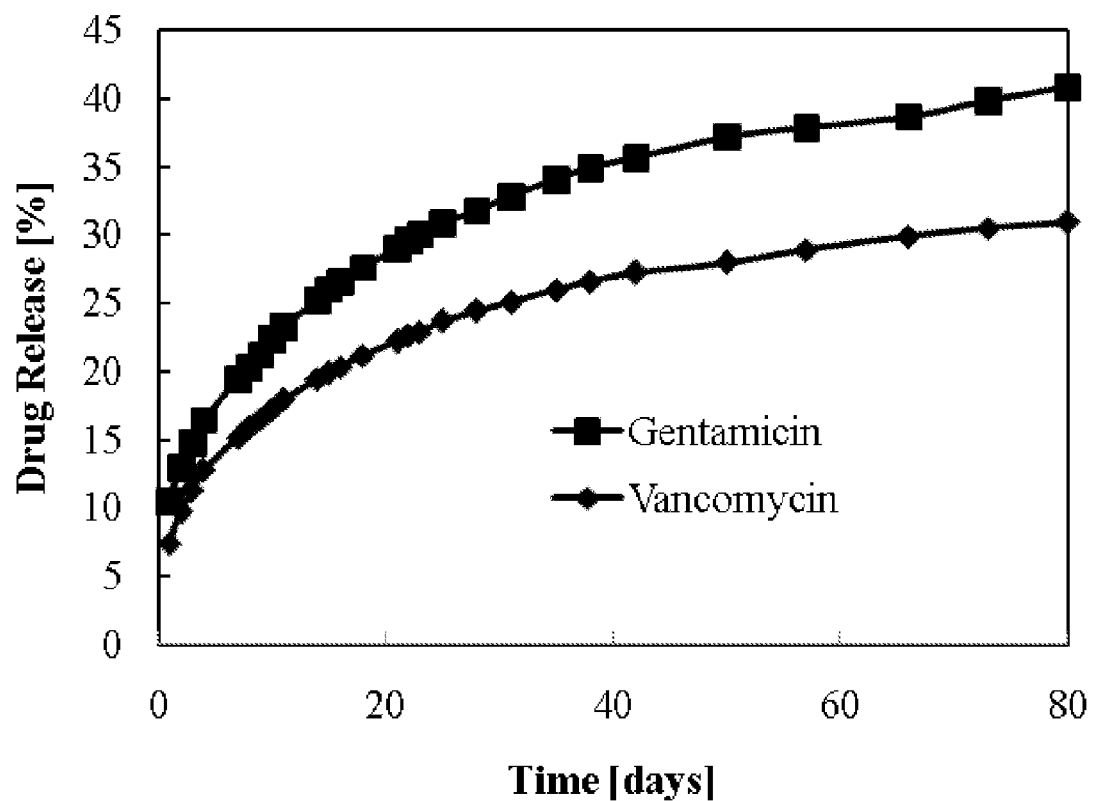
FIG. 13 illustrates the drug release profile of MSN-functionalized bone cement composed of a plurality of antibiotics.

FIG. 13 illustrates the drug release profiles of gentamicin and vancomycin from MSN-functionalized bone cement. After 80 days, the amount of gentamicin and vancomycin released as a percentage to the amount loaded is 40.8% and 31%, respectively. The percentage of gentamicin released from the dual antibiotic loaded bone cement is lower than that of gentamicin alone (70% gentamicin released when loaded alone) However, the drug release efficiencies are still much higher than the current commercially available antibiotic-loaded bone cement which releases only <5% of the total antibiotic loaded for up to 1 day. FIG. 13 demonstrates that a plurality of antibiotics loaded in MSN-functionalized bone cement has improved drug releasing properties using the novel mesoporous silica nanoparticles in bone cement of the present invention.

Example 6
Mesoporous Material Incorporated Bone Cement Containing Antibiotics and Anti-Inflammatory Agents The compositions and methods of the present invention can be applied for prepare MSN formulated bone cement consisting of a plurality of antibiotics and anti-inflammatory agents. As a non-limiting example, the present invention finds utility in the encapsulation of one or a plurality of antibiotics and/or one or a plurality of non-steroidal anti-inflammatory drug agents into MSN functionalized bone cement in order to provide resistance to potential infection and reduction of inflammation from bone replacement surgery. A typical dual action MSN-functionalized bone cement is comprised of a combination of antibiotics, non-steroidal anti-inflammatory drugs and commercially available bone cement. For example, it is made by firstly encapsulating one or a plurality of antibiotics into MSN-PMMA powder in aqueous solution, and secondly encapsulating one or a plurality of anti-inflammatory drugs.

In a non-limiting protocol, 0.30 g of MSN was dispersed in 4 ml of aqueous solution containing 0.10 g of gentamicin. Subsequently, 2.0 g of the composite bone cement powder was immersed into the aqueous suspension to form slurry under stirring. The slurry was dried under vacuum at room temperature. The dried powder was impregnated with 0.10 g of ibuprofen dissolved in ethanol. The wet mixture was dried under vacuum at room temperature again. The obtained mixture of antibiotics and ibuprofen containing solid was ground to fine powder. The samples of antibiotic and ibuprofen loaded bone cement were prepared by mixing the powder with the liquid monomer in a ratio of 2 g/ml in a bowl in a laminar flow hood, in accordance with the manufacturer's instructions. Monomer liquid was added to the polymer-MSN mixture in a bowl and was stirred using spatula until the powder was fully wetted. The soft mixture was inserted into the mold with dimension of 6 mm in diameter and 12 mm in height. The filled mold was pressed between two glass plates for harden overnight at room temperature. Non-limiting examples of analgesics or anti-inflammatory drugs include steroid agents (e.g., substances related to cortisone, like methyprednisolone acetate) and non-steroidal agents (e.g., acetylsalicyclic acid, acetaminophen, celecoxib, refecoxib, ibuprofen and indomethacin).

Figure 14:
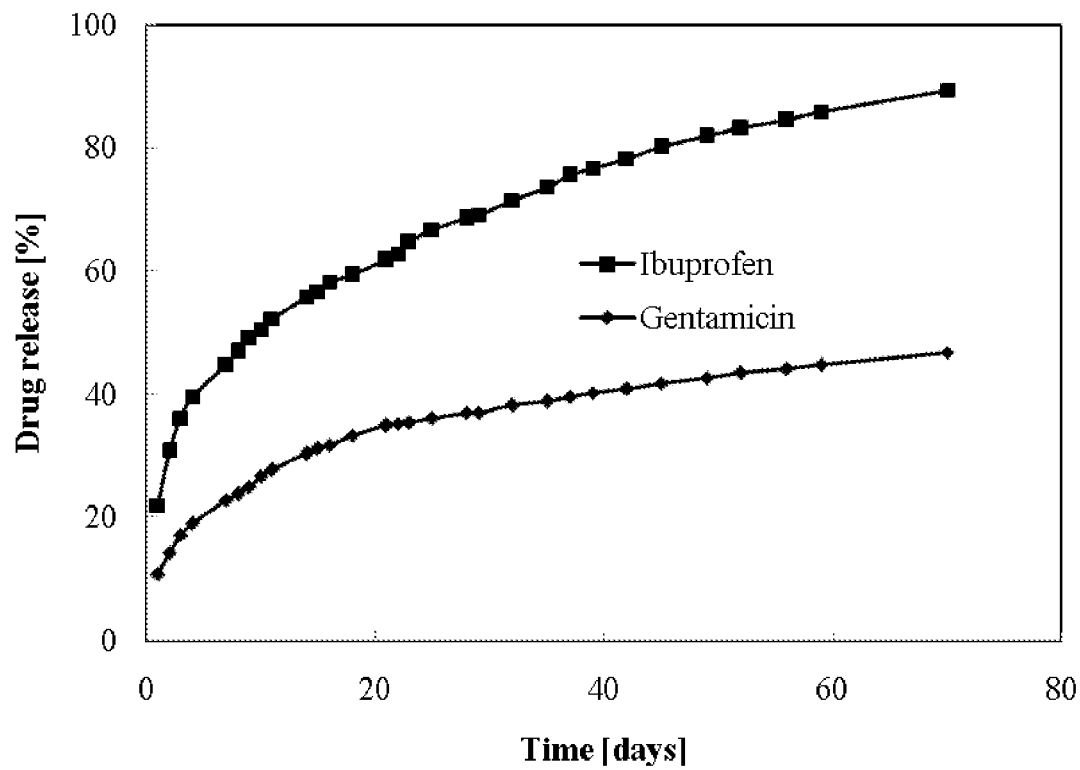
FIG. 14 illustrates the drug release profile of MSN-functionalized bone cement composed of a plurality of active pharmaceutical agents.

FIG. 14 shows the drug release profiles of ibuprofen and gentamicin from dual drug-loaded MSN functionalized bone cement. Over the course of 70 days, the percentage of gentamicin and ibuprofen released is 90% and 47%, respectively. The release of gentamicin in the presence of ibuprofen is reduced, compared to gentamicin alone. The smaller molecular size of ibuprofen and its location on the outer surfaces of the nanoparticles may account for the higher release rate. The composition described in this example is useful for the treatment of infection and inflammation from bone replacement surgery.

Figure 15:
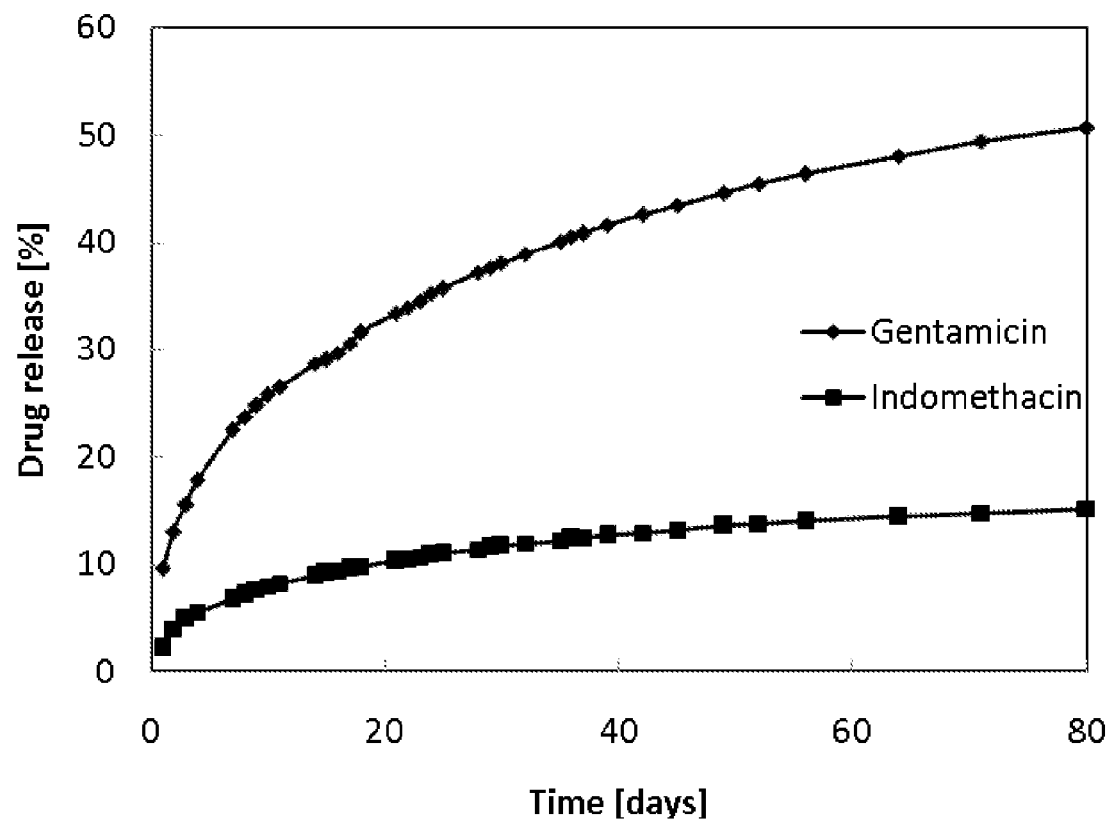
FIG. 15 illustrates the drug release profile of MSN-functionalized bone cement composed of gentamicin and indomethacin.

FIG. 15 shows the drug release profiles of indomethacin and gentamicin from dual drug-loaded MSN functionalized bone cement. Indomethacin has very poor solubility (0.004 mg/mL) in $H_2O$ at 20° C. Although the indomethacin solution used during encapsulation is at saturation, only 15% is released from the bone cement. On the other hand, 51% of the gentamicin encapsulated in MSN-formulated bone cement is released in 80 days. The percentage of antibiotic released remains much higher than that of commercial antibiotic-loaded bone cement.

Example 7
Antibiotic Loaded Mesoporous Nanomaterials Incorporated Bone Cement

This examples illustrates nanomaterials and nanoparticles encapsulating antibiotics and embedded in commercially available bone cement. The compositions and methods of the present invention can be applied to drug loaded mesoporous nanomaterial functionalized bone cement. As a non-limiting example, the present invention finds utility in the encapsulation of active pharmaceutical agents in mesoporous nanomaterial functionalized bone cement in order to provide resistance to potential infection upon bone replacement. Examples of mesoporous materials include, without limitation, mesoporous silica nanoparticles, alumina nanofibers, carbon nanotubes, titania nanotubes, hydroxyapatite nanorods, hydroxyapatite nanoparticles, and a combination thereof.

Figure 16:
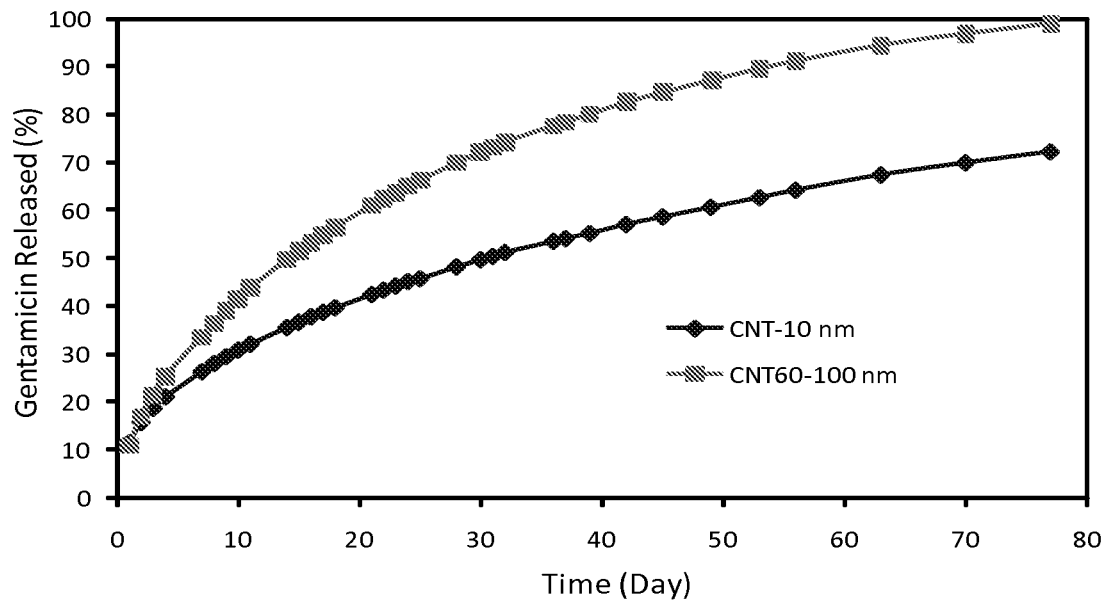
FIG. 16 illustrates the drug release profiles of gentamicin loaded carbon nanotubes-functionalized bone cement.

In this example, gentamicin is loaded into carbon nanotubes of the length of 10 nm or of the range of 60-100 nm. The encapsulated carbon nanotubes (loaded with 3.2 wt % gentamicin) embedded in PMMA-based bone cement form a diffusion matrix that supports sustained release of active pharmaceutical agent. FIG. 16 illustrates the detectable release of gentamicin loaded carbon nanotube formulated SmartSet HV bone cements.

Figure 17:
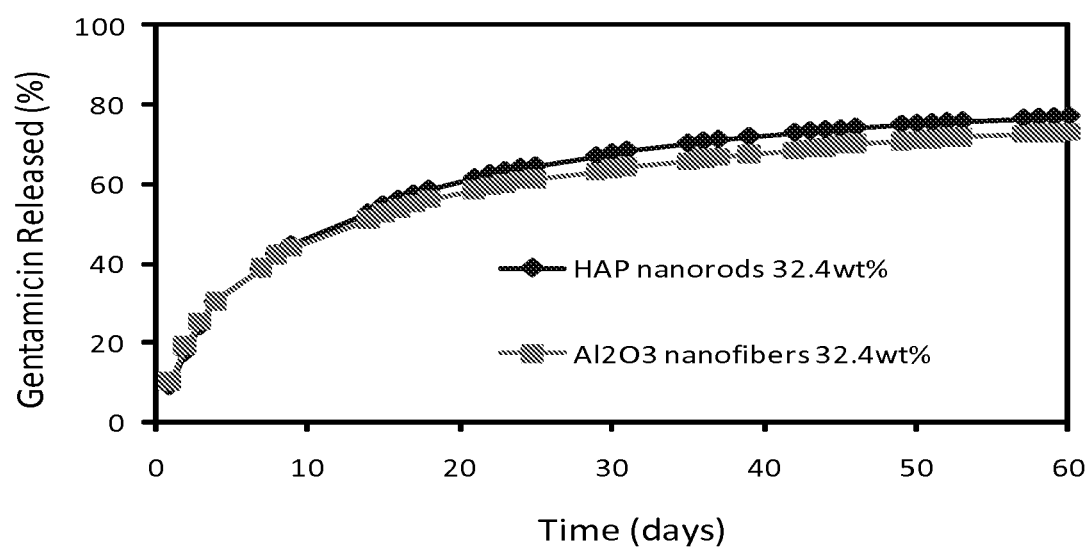
FIG. 17 illustrates the gentamicin release profiles of composite bone cements formulated with either hypoxyapatite nanorods or alumina nanofibers.

In this example, composite bone cement formulated with hypoxyapatite nanorods or alumina nanofibers loaded with 4.85 wt % gentamicin steadily releases active drug for up to 60 days. FIG. 17 shows the sustained release of gentamicin from loaded nanomaterial formulated SmartSet HV bone cements. FIG. 18 shows that the nanomaterial formulated bone cements do not alter the levels of cytotoxicity as compared to non-toxic control bone cement.

Figure 19:
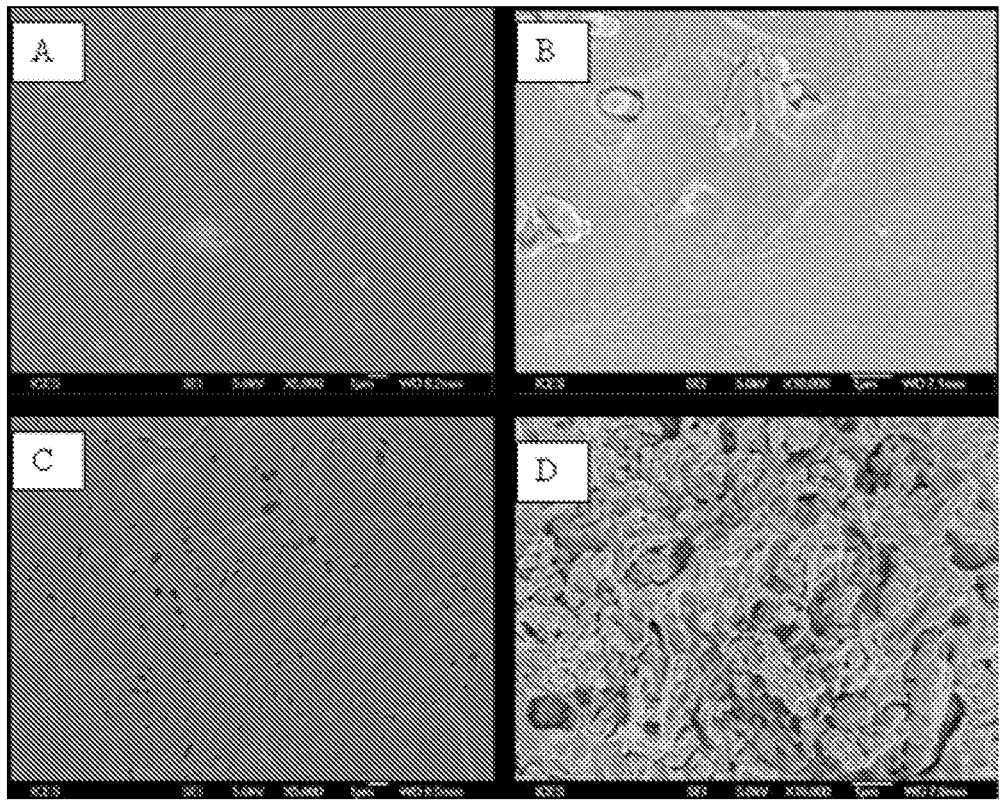
FIG. 19 shows SEM images of: (A) the external surface and (C) the fracture surface of Simplex-P bone cement; compared to (B) the external surface and (D) fracture surface of inventive sample B-1.

Example 8
Scanning Electron Microscope (SEM) Comparison of Simplex-P and MSN Functional Bone Cement FIG. 19 compares the morphology of original Simplex-P (commercially available) and MSN functional bone cement (B1 inventive, Table 3). Both of external and fracture surface were examined by SEM measurement. It is observed that either external or fracture surface of the original Simplex-P bone cement is smooth and condensed. (see, FIGS. 19 A and 19C). As a comparison, a large number of submicron sized pores are formed on the external surface of MSN functionalized bone cement and the micron porosity structure is also observed on the fracture surface. (see, FIGS. 19 B and 19D). The microstructure and small pore size created by the incorporation of MSN into PMMA matrix facilitates the release of antibiotics compared with original PMMA bone cement. The mesoporous incorporated bone cement comprises diffusion channels in a PMMA matrix to facilitate drug molecules diffusion. The small pore size also contributes to the controlled sustained release.

All publications and patent applications cited in this specification are herein incorporated by reference as if each individual publication or patent application were specifically and individually indicated to be incorporated by reference. Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed is:

1. A bone cement, the bone cement comprising:
    a polyacrylate; and
    an active pharmaceutical ingredient, wherein the active pharmaceutical ingredient is an antibiotic and is disposed within mesoporous silica nanoparticles;
    wherein the mesoporous silica nanoparticle content is from 6 to about 10% w/w; and
    wherein the mesoporous silica nanoparticles form a diffusion network.

2. The bone cement of claim 1, wherein the polyacrylate comprises polymerized methyl methacrylate.

3. The bone cement of claim 2, wherein the polyacrylate is poly(methyl methacrylate) or methyl methacrylate copolymer.

4. The bone cement of claim 2, wherein said polyacrylate is a member selected from the group consisting of methyl methacrylate copolymer and methyl methacrylate-styrene copolymer.

5. The bone cement of claim 2, wherein said bone cement comprises diffusion channels in a PMMA matrix to facilitate drug molecules diffusion.

6. The bone cement of claim 1, wherein the mesoporous silica nanoparticles are rod-like.

7. The bone cement of claim 1, wherein the active pharmaceutical ingredient is present in an amount about 0.1 to about 30% w/w.

8. The bone cement of claim 1, wherein the active pharmaceutical ingredient is present in an amount about 1 to about 20% w/w.

9. The bone cement of claim 1, wherein the active pharmaceutical ingredient is present in an amount about 4 to about 15% w/w.

10. The bone cement of claim 1, wherein the antibiotic is selected from the group consisting of an aminoglycoside antibiotic, a glycopeptide antibiotic, a macrolide antibiotic, and a combination thereof.

11. The bone cement of claim 10, wherein the antibiotic is selected from the group consisting of erythromycin, gentamicin, tobramycin, vancomycin, and a combination thereof.

12. The bone cement of claim 11, wherein the antibiotic is gentamicin.

13. The bone cement of claim 11, wherein the antibiotic is a combination of at least two compounds selected from the group of erythromycin, gentamicin, tobramycin, and vancomycin.

14. A method for preparing a bone cement, said method comprising:
    impregnating mesoporous silica nanoparticles with an active pharmaceutical agent to produce an impregnated mesoporous material, wherein the active pharmaceutical ingredient is an antibiotic;
    mixing the impregnated mesoporous material with polyacrylate to produce an admixture, wherein the mesoporous silica nanoparticles content is from 6 to about 10% w/w;
    adding a monomer to the admixture; and
    polymerizing the admixture to form the bone cement.

15. A method for preparing a bone cement, the method comprising:
    impregnating mesoporous silica nanoparticles with an active pharmaceutical agent which is an antibiotic and a polyacrylate to produce an admixture, wherein the mesoporous silica nanoparticles content is from 6 to about 10% w/w;
    adding a monomer to the admixture; and
    polymerizing the admixture to form the bone cement.

16. A method for reducing postoperative osteomyelitis, the method comprising the step of: applying the bone cement of claim 1 to bone.

17. The bone cement of claim 1, wherein the active pharmaceutical ingredient is present in an amount about 0.2 to about 20% w/w.

18. The bone cement of claim 1, wherein the active pharmaceutical ingredient is present in an amount about 0.5 to about 10% w/w.

19. The bone cement of claim 1, wherein the active pharmaceutical ingredient is present in an amount about 1 to about 4% w/w.

\* \* \* \* \*